(12) United States Patent
Wojdas et al.

(10) Patent No.: US 8,570,525 B2
(45) Date of Patent: Oct. 29, 2013

(54) APPARATUS FOR OPTICAL FREQUENCY DOMAIN TOMOGRAPHY WITH ADJUSTING SYSTEM

(75) Inventors: Pawel Wojdas, Zawiercie (PL);
Grzegorz Slusarczyk, Chorzów (PL);
Tomasz Bajraszewski, Torun (PL);
Maciej Wojtkowski, Boniewo (PL);
Anna Szkulmowska, Bydgoszcz (PL);
Piotr Targowski, Torun (PL); Andrzej Kowalczyk, Torun (PL)

(73) Assignee: Optopol Technology S.A., Zawiercie (PL)

( * ) Notice: Subject to any disclaimer, the term of this patent is extended or adjusted under 35 U.S.C. 154(b) by 521 days.

(21) Appl. No.: 12/441,686

(22) PCT Filed: Jun. 22, 2007

(86) PCT No.: PCT/IB2007/052440
§ 371 (c)(1),
(2), (4) Date: Mar. 17, 2009

(87) PCT Pub. No.: WO2007/148310
PCT Pub. Date: Dec. 27, 2007

(65) Prior Publication Data
US 2009/0262359 A1    Oct. 22, 2009

(30) Foreign Application Priority Data

Jun. 23, 2006 (EP) .................................. 06461008
Jun. 7, 2007 (EP) .................................. 07465003

(51) Int. Cl.
*G01B 9/02* (2006.01)
(52) U.S. Cl.
USPC ......................................................... 356/456

(58) Field of Classification Search
USPC .......................... 356/479, 497, 454, 456, 455
See application file for complete search history.

(56) References Cited

U.S. PATENT DOCUMENTS

| 2005/0018201 A1 | 1/2005 | de Boer et al. |
| 2005/0036150 A1 | 2/2005 | Izatt et al. |

(Continued)

FOREIGN PATENT DOCUMENTS

| GB | 2416451 A | 1/2006 |
| WO | WO-2004/043245 | 5/2004 |

(Continued)

OTHER PUBLICATIONS

Choi et al., "Frequency-comb-based interferometer for profilometry and tomography" Optics Letters, OSA, Optical Society of America, Washington, DC, US, vol. 31, No. 13, Apr. 13, 2006, pp. 1976-1978, refer to in the International Search Report.

*Primary Examiner* — Tarifur Chowdhury
*Assistant Examiner* — Jonathan Hansen
(74) *Attorney, Agent, or Firm* — Rabin & Berdo, P.C.

(57) ABSTRACT

In an apparatus for imaging of objects by applying optical frequency domain tomography and provided with an adjusting system for setting a relative position of photosensitive elements (174) and a spectrum image (273), the adjusting system is an automatically controlled device causing a relative displacement of at least one photosensitive element (174) of the detection device (173) of the spectrum and the spectrum image (273) between each other. The adjusting system comprises at least one actuator (14, 16) acting on the dispersion device (171) and/or the set of optical elements (172) and/or the detection device (173) and movement of which causes the relative displacement between each other of at least one photosensitive element (174) of the detection device (173) of the spectrum and the spectrum image (273) of the resultant light beam (270).

5 Claims, 25 Drawing Sheets

(56) References Cited

U.S. PATENT DOCUMENTS

| | | |
|---|---|---|
| 2005/0128488 A1* | 6/2005 | Yelin et al. .................... 356/496 |
| 2006/0066869 A1* | 3/2006 | Ueno et al. .................... 356/497 |
| 2006/0158353 A1 | 7/2006 | Tseng |
| 2007/0002327 A1* | 1/2007 | Zhou et al. .................... 356/456 |
| 2007/0127033 A1 | 6/2007 | Ueno |

FOREIGN PATENT DOCUMENTS

| | | |
|---|---|---|
| WO | WO-2006/017837 A2 | 2/2006 |
| WO | WO-2006/019181 | 2/2006 |
| WO | WO-2006/036717 | 4/2006 |
| WO | WO-2007/003288 | 1/2007 |
| WO | WO-2007/016296 | 2/2007 |
| WO | WO-2007/084750 | 7/2007 |

* cited by examiner

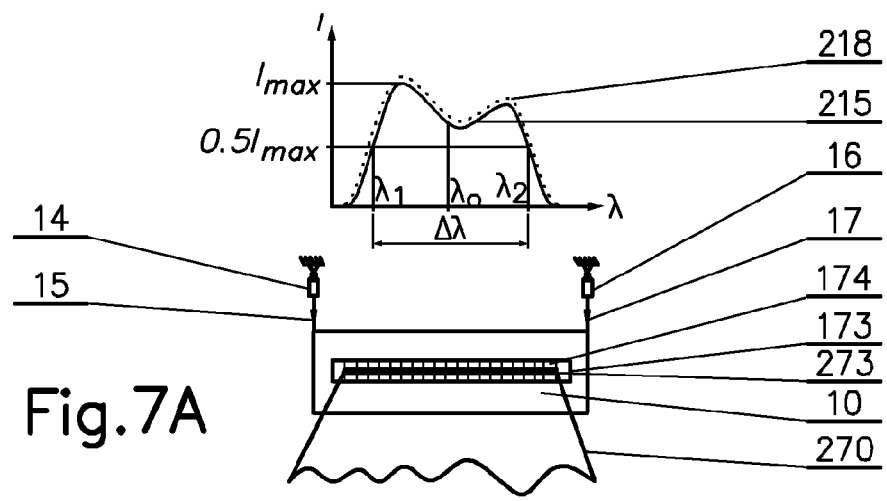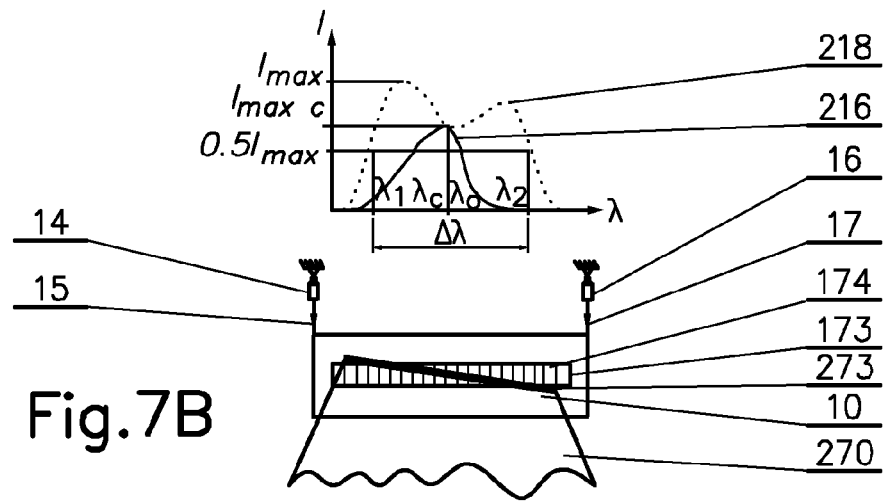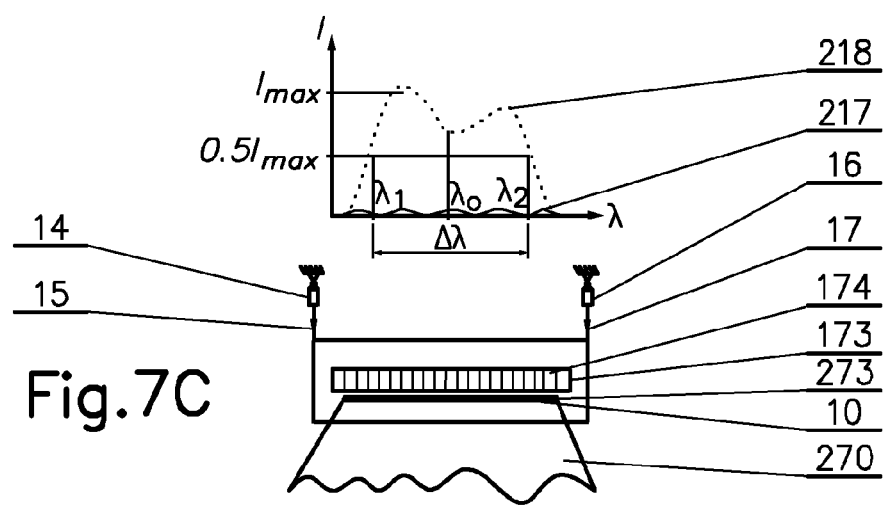

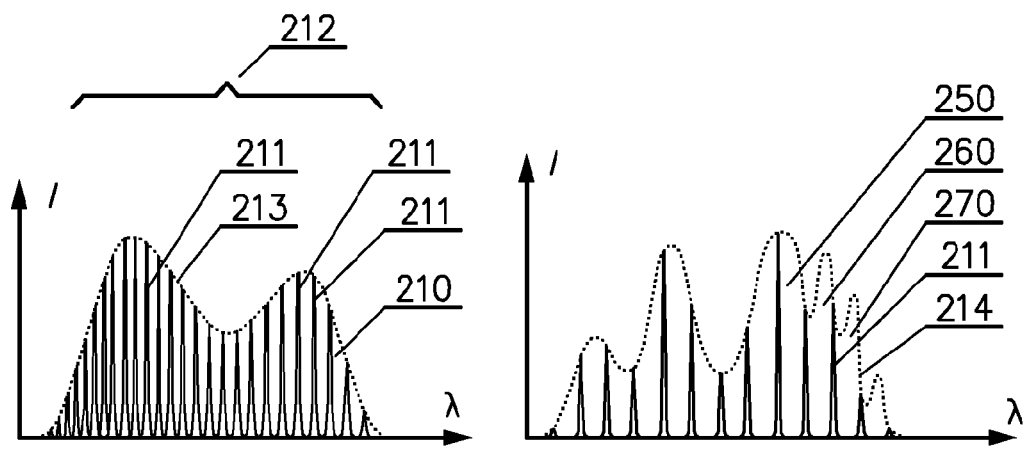
Fig.15    Fig.16
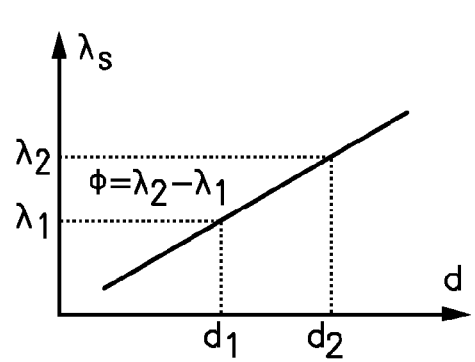 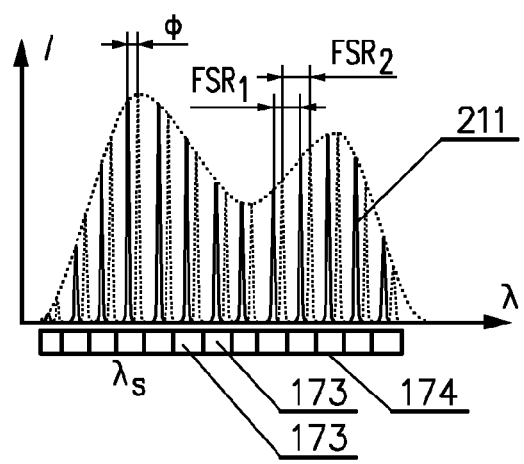
Fig.17    Fig.18

APPARATUS FOR OPTICAL FREQUENCY DOMAIN TOMOGRAPHY WITH ADJUSTING SYSTEM

TECHNICAL FIELD

The present invention relates to an apparatus for optical frequency domain tomography with an adjusting system, an adjusting system of apparatus for optical frequency domain tomography and a method for adjusting an apparatus for optical frequency domain tomography and a method for imaging of objects

BACKGROUND ART

Optical tomography is an imaging technique of objects and their internal structure that is based on analysis of a signal created from a light reference beam and a light object beam, which is back-scattered by object internal structures and interferences with the light reference beam and forms a resultant light beam. The resultant light beam is directed onto a dispersion device, for example a diffraction grating, and then is registered by a detection device or a spectrum recorder, for example, a matrix of photosensitive elements used in a linear CCD camera. The electrical signal in a form of a digital signal generated by the matrix is transmitted to a calculation unit and information about the axial structure of the object being examined is received by means of numerical calculation in the calculation unit, for instance by means of a PC.

Apparatuses to produce imaging of objects by means of optical tomography are known in numerous variants. For example, a method for fast object imaging using spectral optical tomography in which, to increase the speed of object imaging, a matrix of sensitive elements with a memory to store information about scanned fragments of the object is described in the publication of international application No. WO 2004/043245 A1.

From the paper entitled "Full range complex spectral optical coherence tomography," M. Wojtkowski, A. Kowalczyk, R. Leitgeb, and A. F. Fercher, *Opt. Lett.* 27, 1415-1418 (2002) is known a method for imaging the interior structure of objects, in which two or more spectrum measurements at each position of the object light beam may be performed.

In turn, the publication of international patent application No. WO 2006/017837 A2 describes a process, system and software arrangement to determine at least one position of one portion of sample using an optical coherence tomography.

Additionally, from the publication of international patent application No. WO 2006/036717 A2 is known an optical feedback between two interferometers for taking desired measurements of length differences of optical paths of two light beams.

Furthermore, the publication of US patent application No. US 2005/0036150 A1 describes a method for imaging of concentration and displacement of a specific agent in an examined object using an optical coherence tomography.

In addition, form the publication of UK patent application No. GB 2416451 A is known a method of detecting images of objects using a laser-scanning microscope with linear scanning.

From the publication No. WO2007003288 of the international application entitled "Fourier domain optical coherence tomography employing a swept multi-wavelength laser and a multi-channel receiver" is known a system, which comprises a swept multi-wave length laser, an optical interferometer and a multi-channel receiver. By employing a multi-wavelength laser, the sweeping range for each lasing wavelength is substantially reduced as compared to a pure swept single wavelength laser that needs to cover the same overall spectral range.

From the publication No. WO2007016296 of the international application entitled "Optical coherence imaging systems having a reduced effective linewidth and methods of using the same" are known frequency domain optical coherence imaging systems, which have an optical source, an optical detector and an optical transmission path between the optical source and the optical detector. The optical transmission path between the optical source and the optical detector reduces an effective linewidth of the imaging system. The optical source may be a broadband source and the optical transmission path may include a periodic optical filter.

Among the above-described, known imaging techniques, based on the optical tomography method, the best results for eye imaging are achieved by SOCT, characterised by high longitudinal resolution, fast measurement speed and high sensitivity. However, the tomography equipment created to date, based on this method, also has the limitations, for instance, the accuracy of imaging of objects depends on adjusting the apparatus to work conditions and regulation that should be carried out after out of tuning of the apparatus due to vibration during transport, change of temperature and new work condition of the apparatus. Nowadays used regulation systems are hand maintained, not precise, time consuming and need to be maintained by users that have been trained in the field of the imaging of objects by means of optical tomography.

Aim of the Invention

The purpose of the invention is to provide an apparatus for optical frequency domain tomography with an adjusting system that allows examining the objects very precisely and can be maintained by users that have no experience in adjusting the apparatuses for optical frequency domain tomography.

DISCLOSURE OF THE INVENTION

The idea of the invention is that in an apparatus for imaging of objects by applying optical frequency domain tomography and provided with an adjusting system for setting a relative position of photosensitive elements and a spectrum image, and comprising a generating device emitting a light beam with a defined spectrum, a means for splitting the light beam into at least one object light beam and at least one reference light beam, a device forming a resultant light beam from at least one reference light beam and at least one object light beam and at least one device for spectral analysis of a light beam with a dispersion device, a set of optical elements, a detection device of the spectrum, the adjusting system is an automatically controlled device causing a relative displacement of at least one photosensitive element of the detection device of the spectrum and the spectrum image between each other, and comprising at least one actuator acting on the dispersion device and/or the set of optical elements and/or the detection device or a displaceable element of the dispersion device and/or the set of optical elements and/or the detection device and movement of which causes the relative displacement between each other of at least one photosensitive element of the detection device of the spectrum and the spectrum image of the resultant light beam formed from at least one reference light beam and at least one object light beam split by the means for splitting the light beam with the defined spectrum emitted by the generating device.

In one of embodiments, the relative displacement of at least one photosensitive element of the detection device of the spectrum and the spectrum image between each other can take place in a plane situated perpendicularly to propagation direction of the resultant light beam.

The entire apparatus being characterized by the feature that the actuator acting on the dispersion device and/or the set of optical elements and/or the detection device or a displaceable element of the dispersion device and/or the set of optical elements and/or the detection device is a mechanism comprising at least one servomechanism controlled by electric signal, and a movable element of the servomechanism is connected mechanically to the dispersion device and/or the set of optical elements and/or the detection device or a displaceable element of the dispersion device and/or the set of optical elements and/or the detection device.

Preferably, the actuator acting on the dispersion device and/or the set of optical elements and/or the detection device or a displaceable element of the dispersion device and/or the set of optical elements and/or the detection device is a mechanism comprising at least one element connected to the dispersion device and/or the set of optical elements and/or the detection device or a displaceable element of the dispersion device and/or the set of optical elements and/or the detection device and the element is displaced by magnetic or electromagnetic field or a force evoked by pressure of fluid, gas or gas mixture, and is connected to the dispersion device and/or the set of optical elements and/or the detection device or to a displaceable element of the dispersion device and/or the set of optical elements and/or the detection device.

Preferably, the generating device emitting the light beam is either a device transforming the light beam with the defined spectrum into a set of components or an optical frequency comb having components spaced at discrete, defined distances, or in a path of the light beam emitted by the generating device is placed a device transforming the light beam into a set of components or an optical frequency comb or optical frequency combs having components spaced at discrete, defined distances, whereas the means for splitting the light beam into at least one object light beam and at least one reference light beam and the device forming the resultant light beam from at least one reference light beam and at least one object light beam are capable to process the optical frequency combs, and the device for spectral analysis of the resultant light beam is provided with the detection device having photosensitive elements capable of registering more than one component of the optical frequency comb, and each of the photosensitive elements of the detection device registers at most one component of the optical frequency comb, and wherein the photosensitive elements of the detection device are spaced at distances correlating with the discrete defined distances between the components of the optical frequency comb.

The device transforming the light beam with the defined spectrum into the optical frequency comb or the set of the optical components can be a Fabry-Perot interferometer or an adjustable or tuned Fabry-Perot interferometer or an etalon or an arrangement basing on modulation of a phase or amplitude of coherence laser light.

Preferably, the Fabry-Perot interferometer or the adjustable or tuned Fabry-Perot interferometer or the etalon is fitted with a positioning device for changing a distance between reflective surfaces.

Preferably, the means for splitting the light beam is either at least one cube or rectangular prism beamsplitter or at least one fiber-coupler or at least one partially-transparent mirror.

In the path of the object light beam can be placed at least one element focusing the object light beam and/or an arrangement adjusting a position of the object light beam relative to the examined object and/or an arrangement to equal the optical path-lengths of the object light beam and of the reference light beam, whereas in the path of the object light beam and/or the reference light beam can be placed at least one optical arrangement modifying a cross-section shape of the object light beam and/or the reference light beam.

Preferably, an object can be placed on an apparatus adjusting a position of the object relative to the object light beam.

Preferably, in the path of the at least one reference light beam is placed a reference mirror having an adjustable position.

Preferably, the device forming the resultant light beam from at least one reference light beam and at least one object light beam is either at least one cube or rectangular prism beamsplitter or at least one fiber-coupler or at least one partially-transparent mirror.

Preferably, the detection device is a matrix or a line of photosensitive elements.

Preferably, the device for spectral analysis of the resultant light beam is provided with a calculation unit for transforming the resultant spectrum into an image of the object.

The device transforming the light beam with a defined spectrum into the optical frequency comb or the set of the optical components having the components spaced at discrete, defined distances can be fitted with a positioning device adjusting the distances between the optical components of the set of the optical components to the distances between the photosensitive elements of the detection device.

The device for spectral analysis of the resultant light beam is fitted with an arrangement for adjusting the distances between the optical components of the set of the optical components to the distances between the photosensitive elements of the detection device.

The idea of the invention is also a system for adjusting an apparatus for imaging of objects by applying optical frequency domain tomography provided with at least one device for spectral analysis of a light beam with a dispersion device, a set of optical elements and a detection device of the spectrum characterised in that it is an automatically controlled device causing a relative displacement of at least one photosensitive element of the detection device of the spectrum and the spectrum image between each other and comprising at least one actuator acting on the dispersion device and/or the set of optical elements and/or the detection device or a displaceable element of the dispersion device and/or the set of optical elements and/or the detection device and movement of which causes the relative displacement of at least one photosensitive element of the detection device of the spectrum and the spectrum image between each other.

In addition, the idea of the invention is that in a method for imaging of objects and a method for adjusting apparatus for optical frequency domain tomography provided with a generating device emitting a light beam with a defined spectrum, a means for splitting the light beam into at least one object light beam and at least one reference light beam, a device forming a resultant light beam from at least one reference light beam and at least one reference light beam, an adjusting system and at least one device for spectral analysis of a light beam formed from a reference light beam and an object light beam and having a dispersion device for splitting a resultant light beam into a spectrum of the resultant light beam, a set of optical elements for forming and/or directing the resultant light beam and a detection device of the spectrum with at least one photosensitive element for registering the spectrum of resultant light beam, at least one photosensitive element of the detection device of the resultant light beam formed from at least one reference light beam and at least one object beam split by the means for splitting the light beam with the defined spectrum emitted by the generating device, and an image of the spectrum is displaced relatively each other using at least one actuator acting on the dispersion device and/or the set of optical elements and/or the detection device or a displaceable element of the dispersion device and/or the set of optical elements and/or the detection device and movement of which causes the relative displacement of at least one photosensitive element of the detection device of the spectrum and the spectrum image of the resultant light beam between each other.

In one advantageous embodiment of the invention, when displacing at least one photosensitive element of the detection device of the resultant light beam and the image of the spectrum relatively each other using the actuator, the detection device and a line of the image of the spectrum is brought to cross each other, and that a point of change-over is determined at the detection device and direction of rotation of at least one photosensitive element relatively to the image of the resultant light beam or rotation of the image of the resultant light beam relatively to at least one photosensitive element is changed after crossing the point of change-over by the line of the image of the spectrum, and that changing the direction of rotation is being done until parameters of registration of the spectrum determined by a manufacturer of the apparatus for optical frequency domain tomography or recognized by a user as sufficient for registration of the spectrum are achieved.

Preferably, the displacing of at least one photosensitive element relatively to the image of the resultant light beam is being done until an electric signal is generated by the detection device, and after determining a point of change-over on the detection device, direction of rotation of at least one photosensitive element of the detection device relatively to the image of the resultant light beam or rotation of the image of the resultant light beam relatively to at least one photosensitive element of the detection device is changed at every crossing the point of change-over by the line of the image of the spectrum, and changing of the direction of rotation is being done until a curve of light intensity I or energy registered by the detection device versus wave length λ achieves a shape corresponding to a shape of a curve of light intensity I or energy of the light emitted by the light source versus wave length λ or area under the curve of light intensity I or energy registered by the detection device versus wave length λ achieves area corresponding to the area under the curve of light intensity I emitted by the light source after taking into account scattering loss.

In further advantageous embodiment of the invention, the light beam has a spectrum comprising a set of optical components and/or forming an optical frequency comb, and that the spectrum of resultant light beam formed from at least one reference light beam and at least one object beam split by the means for splitting the light beam with the defined spectrum emitted by the generating device is registered by the detection device fitted with photosensitive elements spaced at distances correlated with the discrete defined distances of optical components of the resultant light beam and transformed into a data stream enabling the visualization of the examined object.

Preferably, generating the light beam in the form of the optical frequency comb or the set of the optical components is conducted by a Fabry-Perot interferometer or an adjustable or tuned or scanning Fabry-Perot interferometer placed in a generating device emitting the light beam or after the generating device emitting the light beam.

Preferably, generating the light beam as the optical frequency comb or the set of the optical components is achieved by a phase or amplitude modulator placed in a generating device emitting the light beam or after the generating device emitting the light beam.

Preferably, generating the light beam as the optical frequency comb or the set of the optical components is characteristic of the type of light emission for the light source used.

Preferably, a distance between reflective planes of the Fabry-Perot interferometer or the adjustable or tuned or scanning Fabry-Perot interferometer is changed to position successive components of the resultant spectrum, this being the set or group of component modulated by the interference signal, onto every q-th photosensitive element of the detection device, where q>0.

Preferably, an angle between the resultant light beam and the device separating spatially wavelength components is chosen to fit successive components of the resultant spectrum, this being the set or group of component modulated by the interference signal, onto every q-th photosensitive element of the detection device, where q>0.

Preferably, an angle of incidence of the resultant spectrum onto the detection device is chosen to align successive components of the resultant spectrum, this being the set or group of component modulated by the interference signal, onto every q-th photosensitive element of the detection device, where q>0 especially if q=2.

Preferably, from signals generated by components of the resultant spectrum projected onto the detection device, this being the set or group of component modulated by the interference signal, are chosen signals from every q-th photosensitive element of the detection device.

Preferably, transforming spectra into a visual or virtual image of objects is performed by calculating Fourier transformations and imaging all Fourier transformations as a light intensity image.

BRIEF DESCRIPTION OF THE DRAWINGS

The invention will now be described by way of example and with reference to the accompanying drawings in which:

FIGS. 7A, 7B and 7C show location of a spectrum and a matrix at different adjustment states of apparatus for imaging of objects;

FIG. 15 shows a spectrum of a light beam modulated by an optical frequency comb;

FIG. 16 shows a spectrum of a resultant light beam;

FIG. 17 shows dependency of a shifting value φ on a distance d between reflecting planes of an adjustable Fabry-Perot interferometer;

FIG. 18 shows the idea of shifting of components of an optical frequency comb;

BEST MODE FOR CARRYING OUT THE INVENTION

Figure 1:
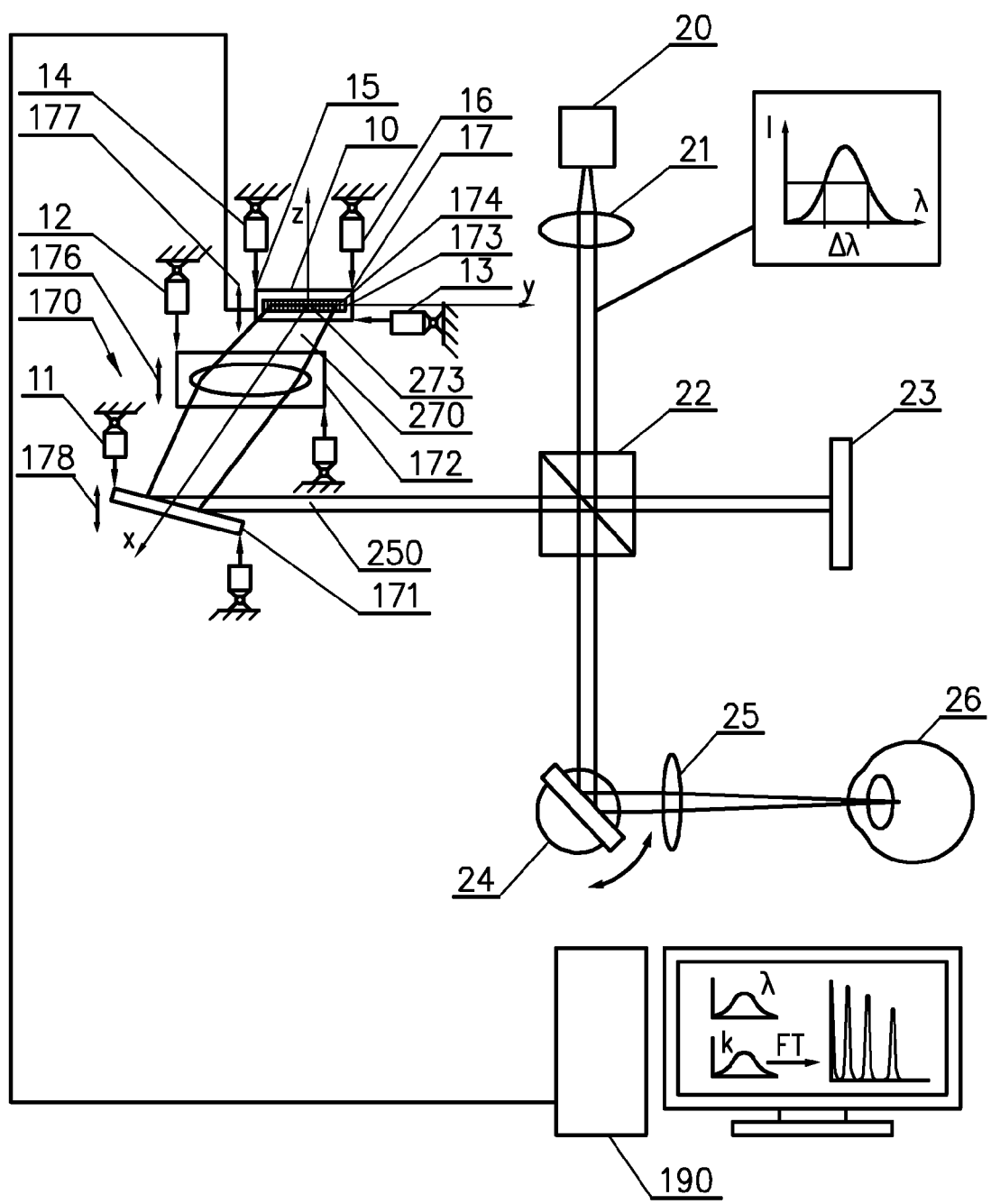
FIGS. 1-6 show block diagrams of different arrangements of apparatus for imaging of objects applying spectral optical coherence tomography.

The embodiments presented in the drawings are intended only for illustrative purpose and do not limit the scope of the invention as defined by the accompanying claims.

FIG. 1 shows an apparatus for optical frequency domain tomography according to present invention, called also an apparatus for optical frequency coherence tomography, provided with an adjusting system. The apparatus for optical frequency domain tomography comprises, among others, a light source 20 emitting a light formed by a collimating lens 21 and then split into two arms by a beam splitter 22. In the object arm the light, directed by a transverse scanning mirror 24 and an object lens 25, penetrates the interior of an object 26, is back-scattered by its internal structures and returns to the beam splitter 22. Simultaneously, light in the reference arm is reflected from a fixed or moveable reference mirror 23 and also returns to the beam splitter 22, in which a resultant beam is created and is registered by a spectrometer 170. In the spectrometer 170, the resultant beam 250 is directed onto a diffraction grating 171, which splits the resultant beam into a spectrum 270 modulated by interference fingers and registered by a detection device 173, for example by a matrix of photosensitive elements 174. An electrical signal, generated by the detection device, for example linear CCD camera type AViiVA M2CL2014 made by Atmel, is transmitted to a calculation unit 190. Information about the axial structure of the object being examined (single image line—A-scan) is received by means of numerical calculation in the calculation unit 190, for instance by means of a PC. After recording a first cross-section, the beam is traversed in the y axis (perpendicular to the x axis) forming a further trace in direction x. As a final result a three dimensional reconstruction of the object is created.

An adjusting system, with which the apparatus for optical frequency domain tomography is provided, and which can be a device 176 to align the optical elements 172, a device 177 to control a position of the detection device 173 as well as a device 178 to control a position of the spectrometer relative to the resultant light beam 250, comprises, among others, at least one working unit or actuator, for instance a servomechanism 11, 12, 13, 14, 16, for example servomechanism type HS-645MG manufactured by Hitec, USA, a moving element of which is mechanically coupled with a moving element of one of above mentioned devices 176, 177 and 178 causing relative moving of at least one photosensitive element 174 of the detection device 173, called also a spectrum recorder, and a spectrum image 273 of the resultant light beam 250 in yz-plane situated perpendicularly to direction of the resultant light beam propagation, in this case, situated perpendicularly to x-axis. The moving element of one of above mentioned devices 176, 177 and 178 can be an end of a supporting element 10 of the detection device, a point of support or an articulated joint 15, 17, with which the working element or doing element of the servomechanism 14, 16, is coupled, and displacement or shift of which is automatically controlled by an electrical signal sent, for instance from the calculation unit 190. The moving element can be also an element displaced by magnetic or electromagnetic field or a force caused by pressure of liquid, gas or a gas mixture.

Figure 2:
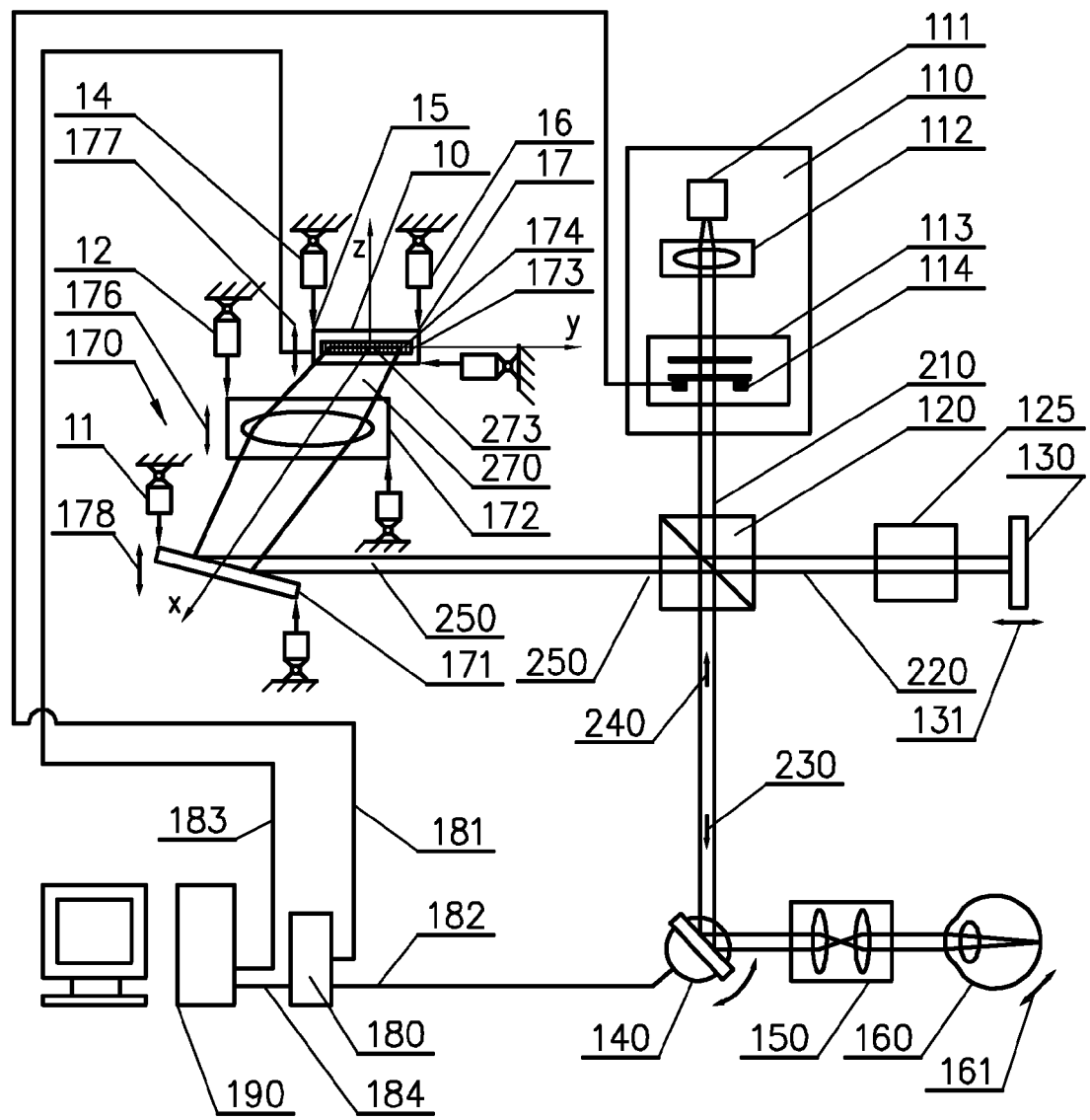

FIG. 2 shows further embodiment of the apparatus for optical frequency domain tomography, which comprises, among others, an optical frequency comb generator 110 emitting a light beam 210 consisting of discrete spectral components equidistantly distributed in optical frequency domain. The generating device or the optical frequency comb generator 110 is provided with a light source 111 emitting a light with low temporal coherence and high spatial coherence with a range or a spectral band $\Delta\lambda$ and a central wave length $\lambda_0$, an optical element 112, such as a collimating lens, and an adjustable or tuned or scanning Fabry-Perot interferometer 113. One of the mirrors of the adjustable Fabry-Perot interferometer 113 is mounted on a positioning device 114 to control positions of the components of the optical frequency comb and/or to adjust distances between the components of the component set to distances between photosensitive elements 174 of the detection device 173, for example a matrix of photosensitive elements. The light beam 210, generated by the generator 110 of the optical components or the optical frequency comb, passes through a beam splitter 120, which splits the light beam 210 into at least one reference light beam 220 and at least one object light beam 230. The reference light beam 220 passes through a system of optical elements 125 to compensate for dispersion in both arms of the apparatus, and is directed to a reference mirror 130 and is then returned by the reference mirror 130. As it returns, the reference light beam again passes through the system of optical elements 125 for compensation of dispersion and again reaches the beam splitter 120.

The object light beam 230 is directed onto an object by an optical system 140 for changing beam direction, in which at least one mirror is mounted on a pivoted mechanism, and by a set of optical elements 150 that forms the object light beam 230, dependant on the selected/specific application and/or polarizes the object light beam 230. For instance, for examination of the eye fundus a set of two lenses in a telescopic arrangement may be applied. A returning object light beam 240, with a circular, elliptical or linear cross-section, back-scattered or reflected from the internal structures of the object 160 with an adjusting system 161, is collected by the set of optical elements 150 and is directed to the beam splitter 120 by the optical system 140 for changing beam direction. The object light beam 240 returning from the object and the reference light beam 220 reflected from the reference mirror 130 with an adjusting device 131 is assembled in the beam splitter 120 into a resultant light beam 250, which is then analysed by the spectrometer 170 consisting of a diffraction grating 171, a system of optical elements 172 forming an arrangement for adjusting the distances between the components of the component set to the distances between the photosensitive elements 174 of the matrix, which may be a component of a detection device 173, for example a CCD device. In the spectrometer 170, the resultant light beam 250 is transformed into a resultant spectrum 270 by a device separating spatially wavelength components such as the diffraction grating 171, and then passes through the system of optical elements 172 and is then displayed on the matrix of photosensitive elements 173, which transforms the displayed spectrum 270 into electrical signals for further analysis. Like to the embodiment shown in FIG. 1, the adjusting system, with which the apparatus for optical frequency domain tomography is provided, can be the device 176 to align the optical elements 172, the device 177 to control a position of the detection device 173 as well as the device 178 to control a position of the spectrometer relative to the resultant light beam 250, comprises, among others, at least one working unit, for instance the servomechanism 11, 12, 14, 16, the moving element of which is mechanically coupled with the moving element of one of above mentioned devices 176, 177 and 178 causing relative moving of at least one photosensitive element 174 of the detection device 173 and the spectrum 273 of the resultant light beam.

Figure 3:
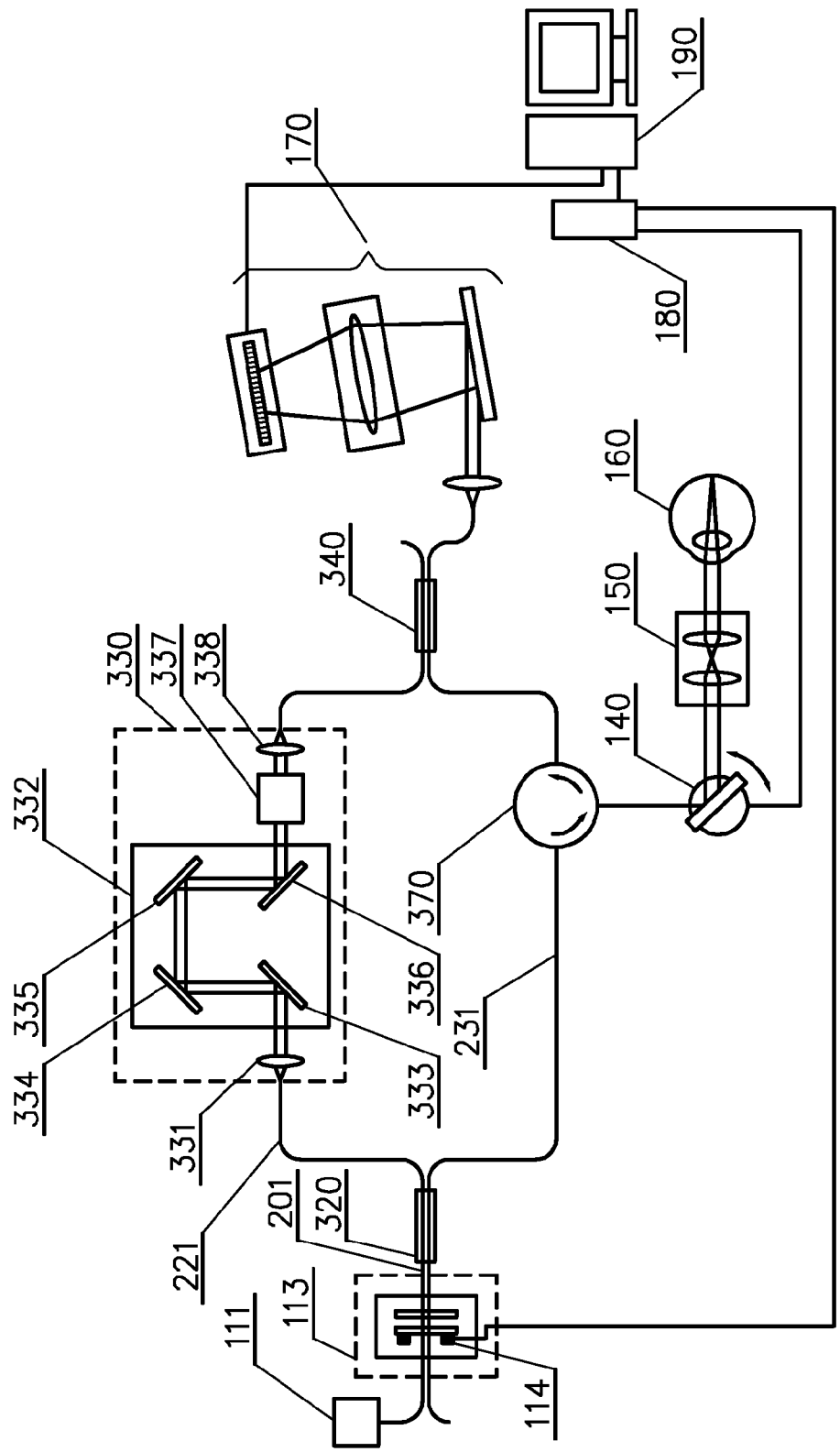

FIG. 3 shows an apparatus without the adjustment system for imaging objects using Fourier domain optical coherence tomography. This is an apparatus for optical frequency domain tomography comprising, among others, an optical frequency comb generator 111 a light beam consisting of discrete spectral components 211, as shown in FIG. 15, equidistantly distributed in optical frequency domain that form an optical frequency comb 212 or a component set having an envelope 213 of a family of components that is directed through maximum values of light intensity of the discrete spectral components 211 in short components, and is displayed as a light-beam spectrum or as a dependency of the light intensity on wave-length $\lambda$. The generating device or the optical frequency comb generator 111 is provided with a light source emitting a light with low temporal coherence and high spatial coherence with a range or a spectral band $\Delta\lambda$ and a central wave length $\lambda_0$ and an adjustable or tuned or scanning Fabry-Perot interferometer 113, which in specific cases is called an etalon that is aligned with the light beam 201 fitted with a positioning device 114 and placed in front of a fiber-coupler. In the fiber-optic configuration, the reference light beam 221 passes through an optical device 330 that forms the reference light beam or passes through the group of optical elements which compensate or correct dispersion in both arms of the interferometer and/or passes a light-polarizer, and next, the reference light beam is directed to a fiber-coupler 340. The optical device 330 may contain an optical element 331 such as a collimator, or a delay system 332, possibly a combination of four mirrors 333-336, a group of optical components 337 for compensation of dispersion in both arms of the apparatus and an optical element 338, such as a focussing lens.

One of the mirrors of the adjustable Fabry-Perot interferometer 113 is mounted on a positioning device 114 to control positions of the components 211 of the optical frequency comb and/or to adjust distances between the components 211 of the component set to distances between photosensitive elements of a matrix, description of which will follow. Such a positioning device might be a piezo-electric element, which is modified after being affected by applied voltage and altering, at the same time, the distance between the mirrors of the adjustable or tuned or scanning Fabry-Perot interferometer 113. If the device is constructed using fiber technology the adjustable Fabry-Perot interferometer is a commercially available device.

The generator 111 of the optical frequency comb or the components set can be made as a light source emitting the optical frequency comb. The generator 111 of the optical frequency comb can also be used with laser light with high temporal coherence with the use of phase or amplitude modulators. Thus, optical components resulting from modulations of the phases of the input light are created.

In turn, the object light beam 231 is directed firstly onto the object 160 to be inspected by a 3-port linear optical circulator 370, the optical system 140 for changing beam direction, in which at least one mirror is mounted on a pivoted mechanism, and by a set 150 of optical elements that forms the object light beam, dependant on the selected/specific application and/or polarizes the object light beam. For instance, for examination of the eye fundus a set of two lenses in a telescopic arrangement may be applied. A returning object light beam, with a circular, elliptical or linear cross-section, backscattered or reflected from the internal structures of the object 160, is collected by the set of optical elements 150 and is directed by the optical system 140 for changing beam direction. The object light beam returning from the object and the reference light beam is assembled in the fiber-coupler 340 into a resultant light beam 250, whose spectrum is shown in FIG. 16. The resultant light beam 250 is then analysed by a device 170 for spectral analysis of a light beam with a dispersion device, for instance a diffraction grating. In the device 170 for spectral analysis, the resultant light beam 250 is transformed into a resultant spectrum 270 by a device separating spatially wavelength components such as the diffraction grating. The resultant spectrum passes through the system of optical elements and is then displayed on the matrix of photosensitive elements, which transforms the displayed resultant spectrum 270 into electrical signals for further analysis.

Figure 31:
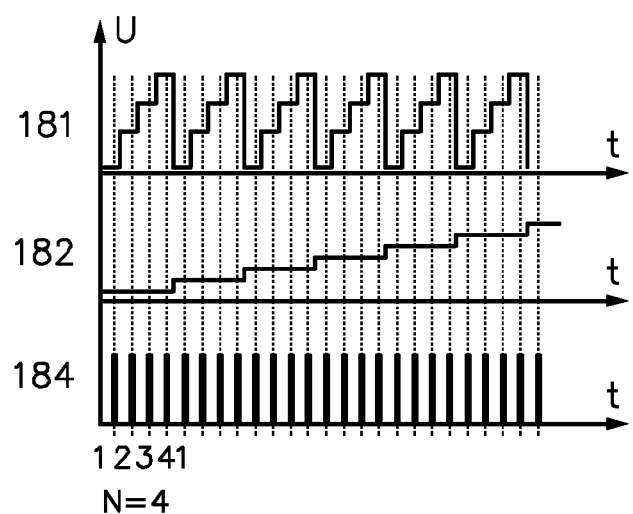
FIG. 31 shows an electrical signal to control of positions of galvanometric mirrors of an optical system for changing light beam direction, an electrical signal to control an adjustable Fabry-Perot interferometer and an electrical signal to a detection device.

Additionally, the apparatus for optical frequency domain tomography within the spectral frequency band contains a control system 180 generating signals 184, shown in FIG. 31, for the generator of the optical components or the optical frequency comb in order to control the positions of the components 211 within the spectrum of the light beam 210. To control the positions of the optical components 211 in the light beam 210, the control system 180 has a signal generator to produce a signal 181 which controls the positioning device 114, for example a piezo-electric element, to vary the distances between the reflective planes of the tuned Fabry-Perot interferometer 113.

Additionally, the control system 180 generates control signals as shown in FIG. 31 to control the optical system 140 for changing light beam direction. This may consist of a set of galvanometric mirrors, changing the direction of the object light beam 230. The control signal 182 sets the galvanometric mirrors that direct the object light beam 230, containing the optical frequency comb 212, onto the object 160 to be examined in a given position.

The device for spectral optical tomography in the domain of optical frequencies also contains a calculation unit 190, for example a PC, which communicates with the control system 180, collects and stores data registered by the CCD device or the detection device and contains software for digital data processing, converting the data into a three dimensional image of the object being examined.

Figure 4:
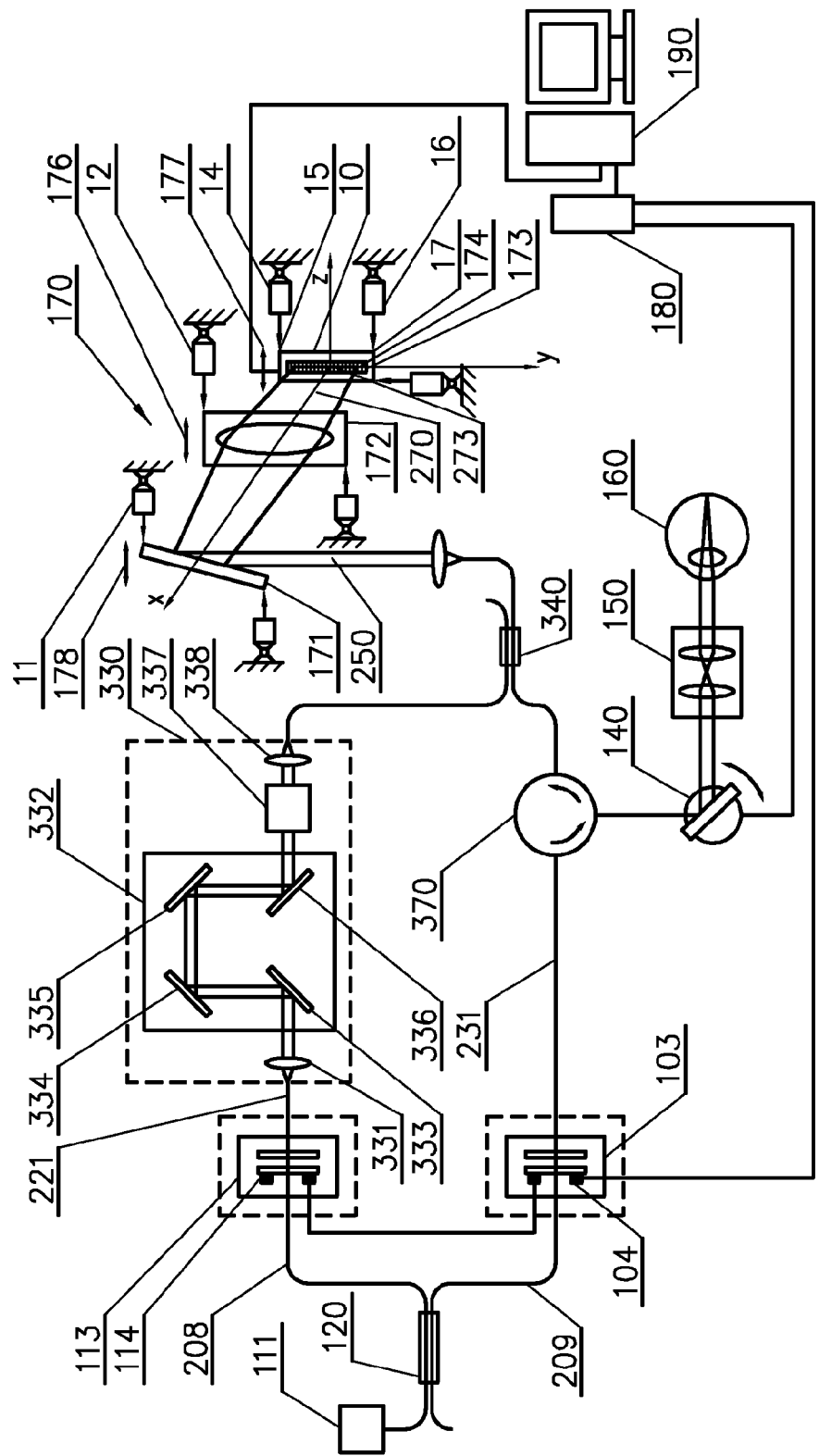

FIG. 4 shows an fiber-optic configuration of the apparatus for optical frequency domain tomography, with the light source 111, the Fabry-Perot interferometers 103, 113 that are fitted with a positioning device 104, 114 and that are aligned with the reference light beam 208 and the object light beam 209. In other embodiment one of Fabry-Perot interferometers can be placed in front of a fiber-coupler 120 in the way of light beam. In the embodiment of the apparatus for optical frequency coherence tomography, which is constructed using fiber technology, the reference light beam passes through an optical arrangement 330 that forms the reference light beam 221 or passes the group of optical elements which compensate or correct dispersion in both arms of the interferometer and/or passes a light-polarizer, and next, the reference light beam is directed to a fiber-coupler 340. The optical arrangement 330 may contain an optical element 331 such as a collimator, a delay system 332, possibly a combination of four mirrors 333-336, a group of optical components 337 for compensation of dispersion in both arms of the apparatus and an optical element 338, such as a focussing lens. In turn, the object light beam 231 is directed onto the object by a linear optical 3-way circulator 370 and the optical system 140 for changing beam direction, and by a set of optical elements 150 that forms the object light beam 230, dependant on the selected application, like in the configuration in the open optics. The optical system 140 for changing beam direction may also be provided with an adjustable light-filter that can be placed in other place, to restrict the intensity of the object light beam during the detection of the background spectrum. The resultant light beam 250, formed from the reference and object light beams, is directed onto the diffraction grating 171, from which as the spectrum 270 is imaged onto the detection device 173.

Additionally, the apparatus for optical frequency domain tomography within the spectral frequency band contain a control system 180 to generate signals for the generating device of the optical components or the optical frequency comb generator to control the positions of the optical components in the light beam as well as a control signal to align the optical system 140, for instance a set of galvanometric mirrors, for changing light beam direction. The control signal sets the galvanometric mirrors that direct the object light beam onto the object 160 to be examined in a given position.

The apparatus for optical frequency domain tomography within the spectral frequency band comprises, beside the calculation unit 190, the adjusting system of the apparatus for optical frequency domain tomography, which can be the device 176 to align the optical elements 172, the device 177 to control a position of the detection device 173 as well as the device 178 to control a position of the spectrometer relative to the resultant light beam 250, comprises, among others, at least one working unit, for instance the servomechanism 11, 12, 14, 16, the moving element of which is mechanically coupled with the moving element of one of above mentioned devices 176, 177 and 178 causing relative moving of at least one photosensitive element 174 of the detecting device 173 and the spectrum 273 of the resultant light beam.

Figure 5:
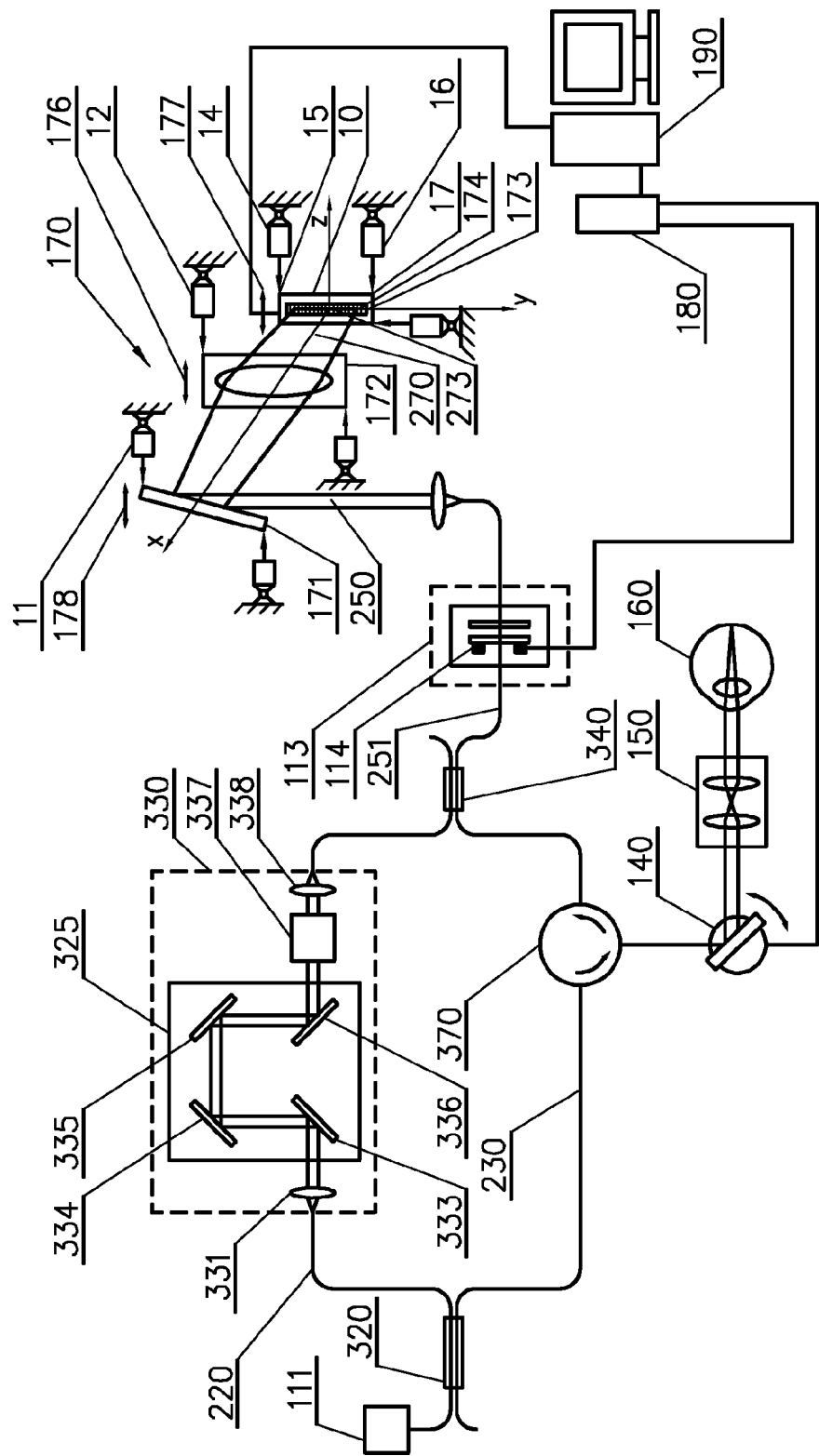

The presented invention shown in FIG. 5 as an embodiment of an apparatus for optical frequency coherence tomography comprises a light source 111, a fiber-coupler 320, an optical arrangement 330 with an optical element 331 such as a collimator, a delay system 325, possibly a combination of four mirrors 333-336, a group of optical components 337 for compensation of dispersion in both arms of the apparatus and an optical element 338, such as a focusing lens for focusing the reference light beam 220. In turn, the object light beam 230 is directed onto the object 160 by a linear optical 3-way circulator 370 and the optical system 140 for changing beam direction, and by a set of optical elements 150 that forms the object light beam 230, dependant on the selected application, like in the configuration in the open optics. The reference and object light beams are directed to the fiber-coupler 320, and then as a beam 251 is directed to the adjustable Fabry-Perot interferometer controlled by the positioning device 114 and to the spectrometer 170, from which as a resultant light beam is directed onto the diffraction grating 171, from which as the spectrum 270 is imaged onto the detection device 173.

Additionally, the apparatus for optical frequency domain tomography within the spectral frequency band contains the control system 180, a calculation unit 190 as well as an adjustment device for adjusting the apparatus for optical frequency domain tomography, which can be the device 176 to align the optical elements 172, the device 177 to control a position of the detection device 173 and/or the device 178 to control a position of the spectrometer relative to the resultant light beam 250, and which comprises, among others, at least one working unit or an actuator, for instance the servomechanism 11, 12, 14, 16, the moving element of which is mechanically coupled with the moving element of one of above mentioned devices 176, 177 and 178 causing relative moving between each other of at least one photosensitive element 174 of the detection device 173 placed on the moving element 10 and the spectrum 273 of the resultant light beam.

Figure 6:
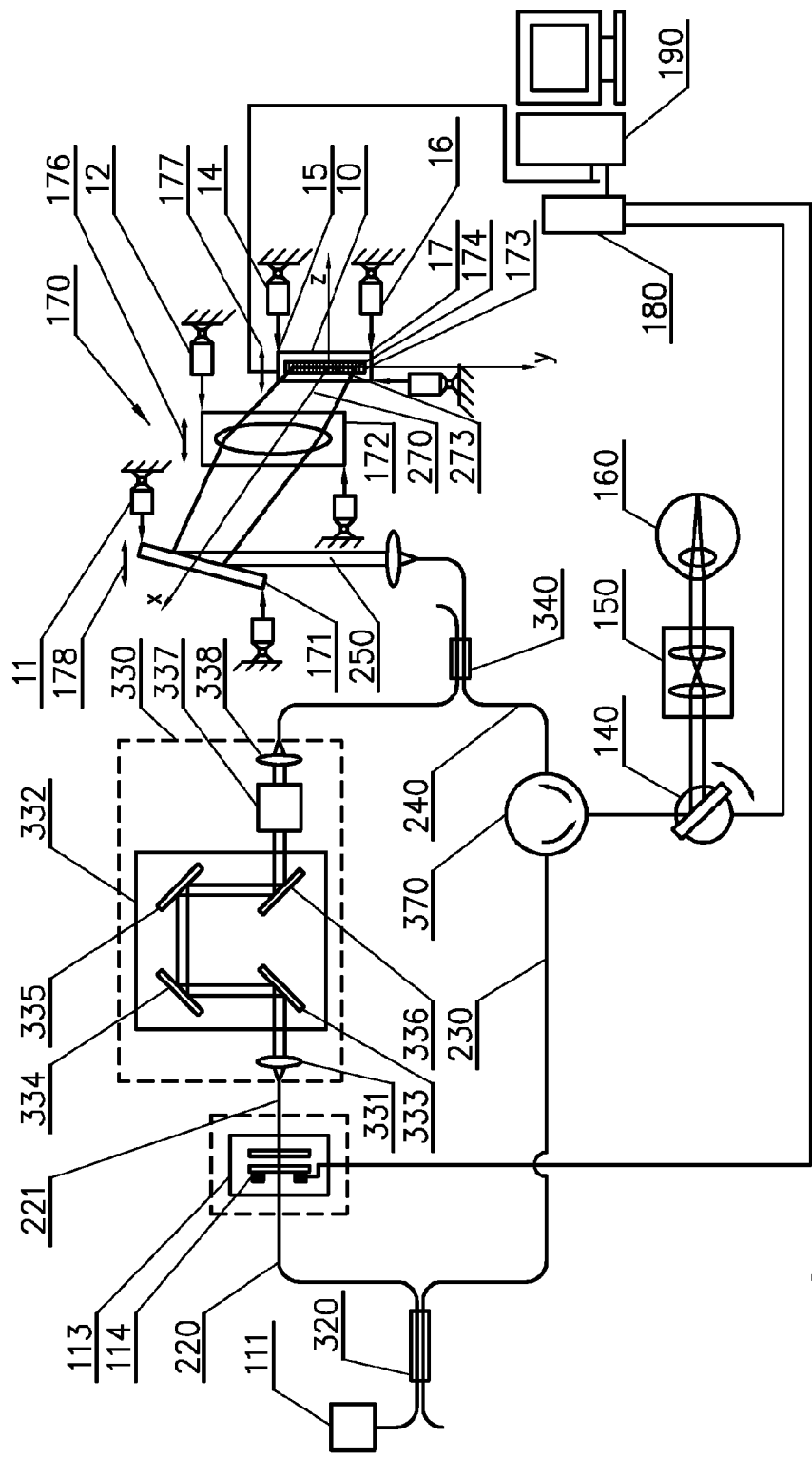

The presented invention, shown in FIG. 6, is an apparatus for imaging objects using optical Fourier domain tomography, also called an apparatus for imaging of objects in coherence light, which comprises a light source 111 and a fiber-coupler 320, which splits the light beam into at least one reference light beam 220 and at least one object light beam 230. The Fabry-Perot interferometer 113 that is fitted with a positioning device 114 and that can be aligned with the reference light beam or the object light beam forms or generates a reference optical frequency light comb 221 or an object optical frequency comb. In the way of the reference light beam is placed an optical arrangement 330 with an optical element 331 such as a collimator, a delay system 332, possibly a combination of four mirrors 333-336, a group of optical components 337 for compensation of dispersion in both arms of the apparatus and an optical element 338, such as a focusing lens for focussing the reference light beam 220. The object light beam 230 is directed onto the object 160 by a linear optical 3-way circulator 370 and the optical system 140 for changing beam direction, and by a set of optical elements 150 that forms the object light beam 230. The reference and object light beams 220, 230, 240 are directed to the fiber-coupler 340, and then to the spectrometer 170. The resultant light beam 250 is directed onto the dispersion device, for instance diffraction grating 171, from which as the spectrum 270 is imaged onto the detection device 173.

The apparatus for optical frequency domain tomography comprises the control system 180, a calculation unit 190 as well as an adjustment system of the apparatus for optical frequency domain tomography, which can be the device 176 to align the optical elements 172, the device 177 to control a position of the detection device 173 as well as the device 178 to control a position of the spectrometer relative to the resultant light beam 250, which comprises, among others, at least one working unit or an actuator, for instance the servomechanism 11, 12, 14, 16, which is mechanically coupled with the moving element of one of above mentioned devices 176, 177 and 178 causing relative moving between each other of at least one photosensitive element 174 of the detection device 173 placed on a supporting element 10 and the spectrum 273 of the resultant light beam.

Independently of a version of the apparatus for imaging of objects by applying optical frequency domain tomography as well as a method for imaging of objects by applying optical frequency domain tomography, before examining the objects, the apparatus for imaging of objects should be adjusted. The biggest technical problem to be solved in the apparatus for imaging of objects by applying optical frequency domain tomography is achieving such position of the matrix of CCD camera, in which the image of the spectrum of the resultant light beam will be situated on the matrix most optimally. In one of the embodiments of the apparatus for imaging of objects by applying optical frequency domain tomography the image of the spectrum can be a line or a rectangle with its width much shorter than its length, as shown in FIGS. 7A, 7B and 7C. Dependently on the degree of adjusting, the image of the spectrum can be in a correct position shown in FIG. 7A, in an oblique position shown in FIG. 7B or in a displacement position shown in FIG. 7C or in an oblique-displaced position, in which no part of the image is projected on the matrix of the detection device. To bring the image 273 of the spectrum to the correct position, a displacement or shifting or rotary devices 14, 16 can be used, whose elements can be moved to achieve a relative displacement of the spectrum image 273 and the detection device 173, called shortly a matrix. These displacement or shifting or rotary devices can be systems basing on a screw joint maintained by hand or displaced by different kind of mechanism controlled electrically, pneumatically or hydraulically. An adjusting system of the apparatus for imaging of objects by applying optical frequency domain tomography, which is the object of the present invention, comprises at least one servomechanism 11, 12, 13, 14, 16 jointed mechanically with a moving element of the dispersion device 171 being a prism or a diffracting grating, and/or the set of optical elements 172, and/or the detection device 173 causing a relative displacement of at least one photosensitive element of the detection device, also called a spectrum register or recorder of the spectrum, and the spectrum image, for instance in a plane perpendicularly situated to propagation direction of the of the resultant light beam.

Structure and a working principle of the adjusting system of the apparatus for imaging of objects will be described by way of example and with reference to the FIGS. 7A, 7B and 7C, which show the adjusting system containing servomechanisms 14, 16, jointed or connected by a point of support or an articulated joint 15, 17 to the supporting element 10 of the detection device 173 created by photosensitive elements 174.

In one of the embodiments, the supporting element 10 of the detection device or photosensitive elements at one end, instead be jointed to one of the servomechanisms, is jointed to a stationary or adjustable element, whose position is handy adjusted. Yz-plane, in which the detection device containing photosensitive elements 174 is displaced, is situated perpendicularly to a propagation direction or an incidence direction of a split light beam 270. In case of an ideal and maximally adjusted optical spectrometer, shown in FIG. 7A, in which a signal has parameters, which suit the user expectation, that means, the signal has parameters allowing a correct work of the apparatus for imaging of objects, the image 273 of the spectrum, being a line, coincidences with the detection device 173 of the CCD camera, which has a shape of a line of photosensitive elements.

It should be noticed, that when the spectrum image has a shape other than a line, there is a possibility to find an axis of symmetry of the spectrum or a line almost similar to the axis of symmetry, which can be called a line of the spectrum image or matrix. In each case the structure and the working principle of the adjusting system of the apparatus for imaging of objects will be the same. In case shown in FIG. 7A, when the spectrum image 273 coincidences with the detection device 173, a curve 215 of light intensity I or energy versus wave length $\lambda$ registered by the detection device has a shape similar to a curve 218 of light intensity I or energy emitted by the light source versus wave length $\lambda$ or area under the curve of light intensity I or energy emitted by the light source achieves maximum possible area corresponding to the area under the curve of light intensity I or energy emitted by the light source after taking into account scattering loss. In this drawing there are shown $I_{max}$ that corresponds to one thousand of units of account, 0.5 $I_{max}$, and $\lambda_1$, $\lambda_2$, at which light intensity I achieves a value of 0.5 $I_{max}$ as well as $\lambda_0$, which is called a central wavelength of the light source waveband. As one thousand of units of account can be also taken a maximum of energy emitted by the light source, which is registered or recorded by the detection device or a maximum of a distribution curve of electric charge generated by the photosensitive elements of the detection device.

FIG. 7B shows a state, in which an electrical signal is present, but its parameters do not answer the expectation, that means, that the resultant light beam 270 has got a contact with the detection device 173, but the apparatus for imaging of objects by applying optical frequency domain tomography needs further adjusting. In this state a curve 216 of light intensity of registered spectrum has momentary maximum $I_{maxc}$ at light wavelength $\lambda_c$, which is shifted in respect to the central wavelength $\lambda_0$ of the light source waveband, and which coincidences with a given photosensitive element, in other words, a pixel, for instance bearing a number 1308. When the momentary maximum $I_{maxc}$ occurs at the central wavelength $\lambda_0$, change-over of direction rotation of the supporting element 10 of the photosensitive elements 174 can take place, and a point, at which the movement direction of the detection device is changed-over, is shortly called a change-over point or a switching over point. The change-over point can be different for different apparatus for imaging of objects by applying optical frequency domain tomography. In practice it is assumed that the change-over point, called also a centre of the light source waveband, at which, during clockwise movement of the detection device or its clockwise rotation of the detection device 173, called shortly a matrix, or in opposite direction, shortly counter-clockwise rotation, the light intensity I has approximately a constant value and the area under the curve of the light intensity changes in a small range. If the centre of the light source waveband appears near by the change-over point, for instance in the range of thirty pixels that answer thirty successive photosensitive elements, then each point appearing in this range of the light wavelength will be taken for a real change-over point.

Additionally, the optical spectrometer can be completely out of adjustment, shown in FIG. 7C, in which no electrical signal can be found or the electrical signal generated by the detection device is so weak that can not be interpreted. The out of adjustment state also appears when not all necessary devices are switched on. When the optical spectrometer is not fully adjusted, the curve 217 of registered light spectrum shows a background, which answers a minimum spectrum or minimum registered power or energy or value of light radiation of surroundings registered by the detection device and which reaches the detection device from different light sources. To adjust the optical spectrometer, the adjusting system should undertake actions that correspond to the state, in which the spectrometer is. In the first step of adjusting it is found in which state the apparatus for imaging of objects is and corresponding algorithms of regulation or adjustment are undertaken. In one of the states, a preliminary roughly adjusting procedure shown in FIG. 9 starts on and the servomechanisms arrange the spectrum image in such position, in which the spectrum image has a contact with the detection device. In the case, when during the preliminary roughly adjusting procedure the electrical signal reaches parameters that answer presumptions, the procedure of adjusting the spectrometer is finished. When a possible maximal adjustment of the apparatus for imaging of objects is required, firstly a search is undertaken to determine parameters that can be reached for a given apparatus for imaging of objects. This is realized when to high parameters are required or set. As the preliminary roughly adjusting procedure is convergent, the apparatus for imaging of objects reaches the maximum parameters and will oscillate around them. Then it is determined if the maximum parameters are reached with previously assumed accuracy, that means, whether parameters of registration of the spectrum image achieve the parameters determined by the manufacturer of the apparatus for optical frequency domain tomography or recognized by a user as sufficient for registration of the spectrum. For example, when the curve of light intensity I versus a wave length λ of the registered spectrum image reaches approximately a shape of the curve of light intensity I versus a wave length λ of the light source, for instance in 99%, or area under the curve of energy or light intensity I registered by the detection device versus wave length λ achieves with accuracy, for instance 1%, area corresponding to the area under the curve of energy or light intensity I emitted by the light source versus wave length λ after taking into account scattering loss.

If current values of energy or light intensity or parameters answer maximum expected values with assumed accuracy, the adjusting system finishes the adjustment, checks whether the reached parameters of adjustment answer the expectations and informs the users of results and their interpretation. When the work of the apparatus for imaging of objects will be disturbed, the adjustment procedure or algorithm will proceed to reach the correct conditions of the work. An adjustment method has been shown by means of flow charts in FIGS. 8-14.

Figure 8:
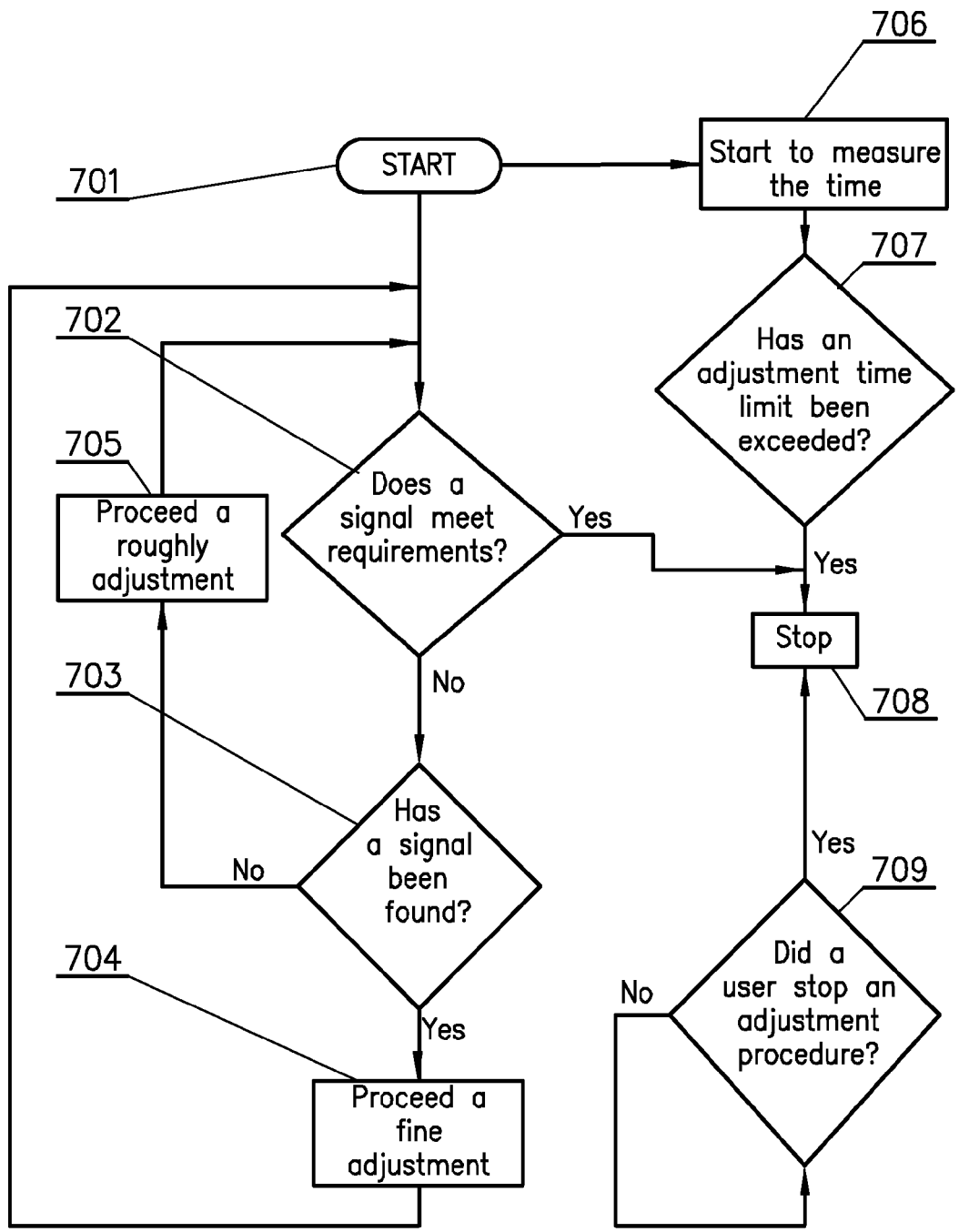
FIG. 8 shows a flow diagram of an adjusting procedure of the apparatus for imaging of objects.
Figure 9:
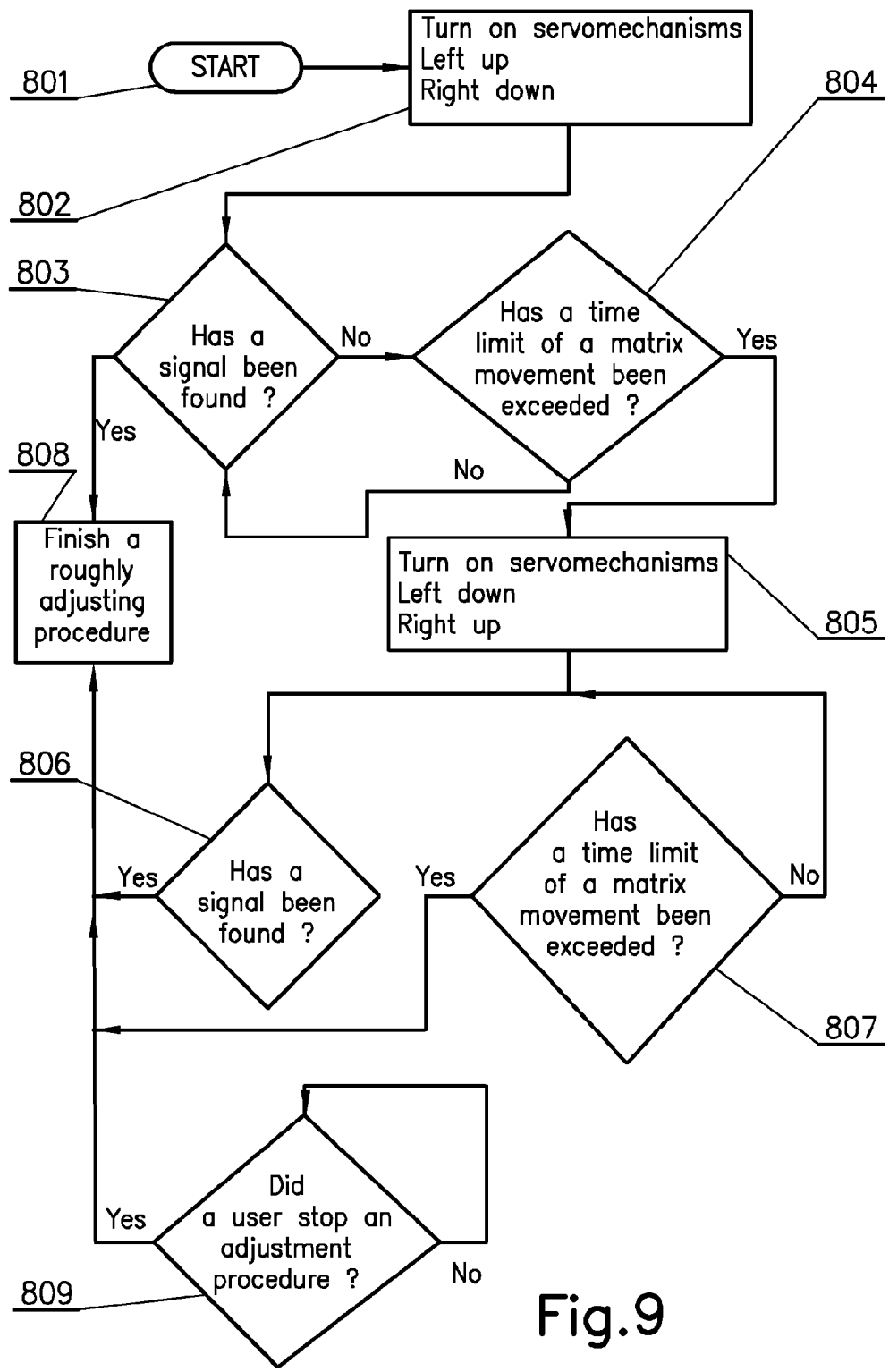
FIG. 9 shows a flow diagram of a preliminary roughly adjusting procedure.

FIG. 8 shows a flow diagram of an adjusting procedure of the apparatus for imaging of objects, which starts in step 701. Simultaneously, in step 706, the procedure starts to measure the time of adjustment and if the adjustment time limit has passed, the adjustment is finished in step 708. Otherwise, in step 702, it is checked if an electric signal generated by the detection device meets requirements. In case, when the electric signal generated by the detection device meets the requirements, the adjustment is finished in step 708. If not, then, in step 703 it is checked if the detection device generates the electric signal and if the signal has been found at all. When there is no signal, a preliminary roughly adjustment shown in FIG. 9 is conducted in step 705, otherwise, when the electric signal has been found, a fine adjustment takes place in step 704, which is shown as a flow diagram in FIG. 10. The user can stop the procedure at any time, and if the user decides to finish the procedure, the procedure is broken by the user in step 709.

The preliminary roughly adjustment, shown in FIG. 9, starts in step 801, when no electric signal has been found in step 703 of the procedure shown in FIG. 8. Next, in step 802, one of servomechanisms is turn on, for instance the left servomechanism, which moves up the supporting element of the detection device, or the right servomechanism, which moves down the supporting element of the detection device or the matrix. During movement of the detection device by one of the servomechanisms, in step 803, it is checked if the detection device generates the electric signal, when the detection device stars to generate the electric signal, the preliminary roughly adjustment is finished and the main adjustment procedure is continued in step 702 of FIG. 8. If the time limit of the roughly adjustment has passed, that is checked in step 804, a change-over of the movement of the detection device takes place in step 805. For instance, when the left servomechanism has moved up the supporting element of the detection device, or the right servomechanism has moved down the supporting element of the detection device, then, the left servomechanism moves down the supporting element of the detection device, or the right servomechanism moves up the supporting element of the detection device in step 805. In step 806 it is checked if the detection device generates the electric signal. When the detection device generates the electric signal, the preliminary roughly adjustment is finished in step 808 and the procedure moves to the step 702 of the main adjustment procedure shown in FIG. 8. When the time limit of the matrix movement has passed, that is checked in step 807, the preliminary roughly adjustment is finished in step 808 and the procedure moves to the step 702, where the adjustment time of this procedure means a movement time of a moved end of the supporting element from one lateral position to the other lateral position, as well as a movement time of the detection device from one lateral position to the other lateral position to assure that the detection device reaches both lateral positions. The user can stop the procedure at any time, and if the user decides to finish the procedure, the procedure is broken by the user in step 809.

Figure 10:
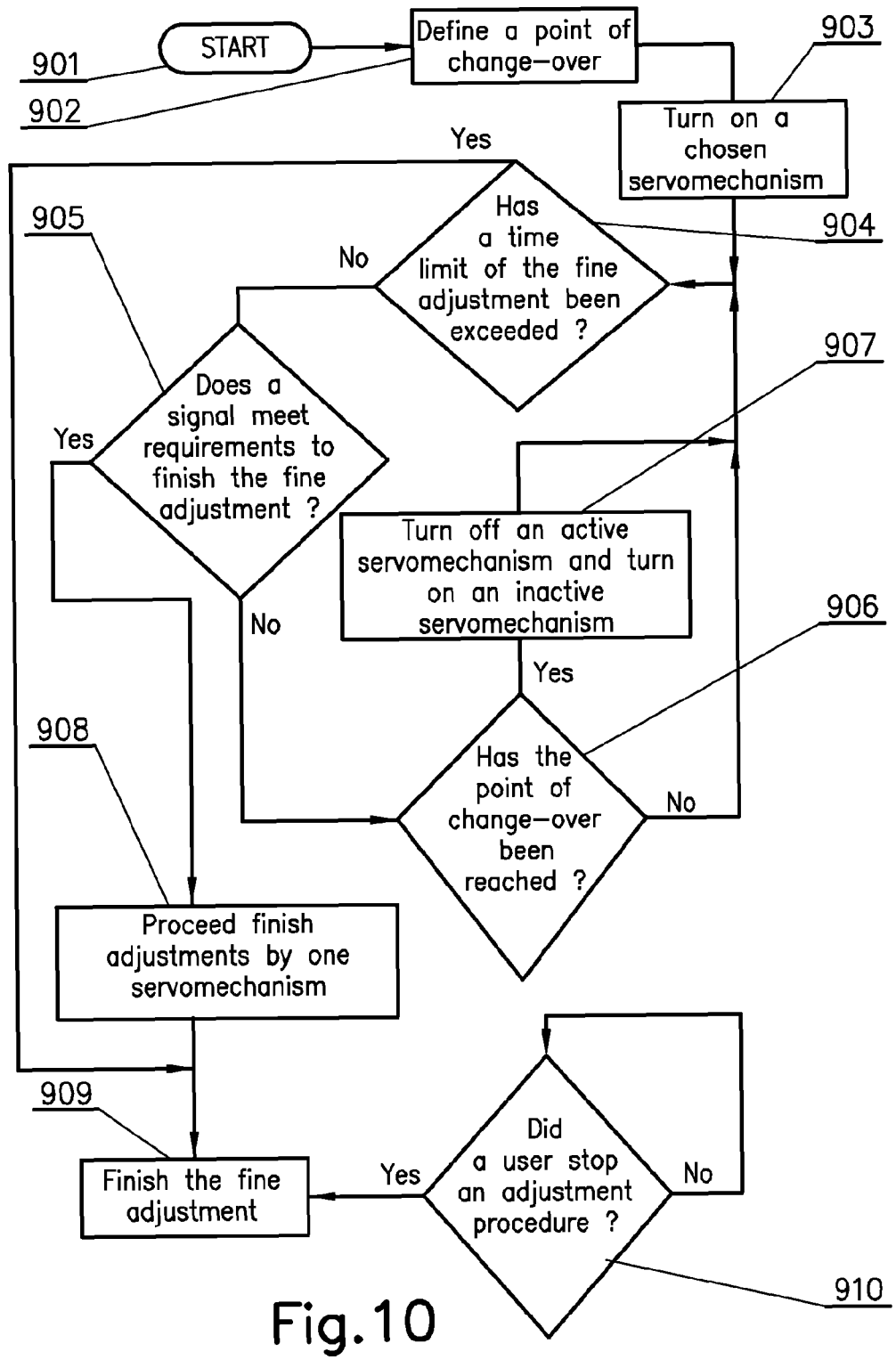
FIG. 10 shows a flow diagram of a fine adjusting procedure.

FIG. 10 shows a flow diagram of a fine adjustment procedure, which starts in step 901, when the electric signal has been found in step 703 of FIG. 8. In step 902 a point of change-over of the movement of the detection device is defined, and then in step 903, a chosen servomechanism is turn on, the right or left servomechanism, which moves up or down the supporting element. If the electric signal generated by the detection device meets the requirements to finish the fine adjustment, what is checked in 905, and then a final adjustment procedure using one servomechanism starts in step 908. The final adjustment procedure is finished in step 909. In case when the electric signal generated by the detection device does not meet the requirements to finish the fine adjustment, in step 906 it is checked whether the point of change-over is reached, and after its crossing, an active servomechanism is turn off and an inactive servomechanism is turn on in step 907. Next, in step 905, it is checked again whether the electric signal generated by the detection device meets the requirements to finish the fine adjustment. The user can stop the procedure at any time, and if the user decides to finish the procedure, the procedure is broken by the user in step 910. The procedure is also finished when the adjustment time limit has passed. The adjustment time is measured in step 904.

Figure 11:
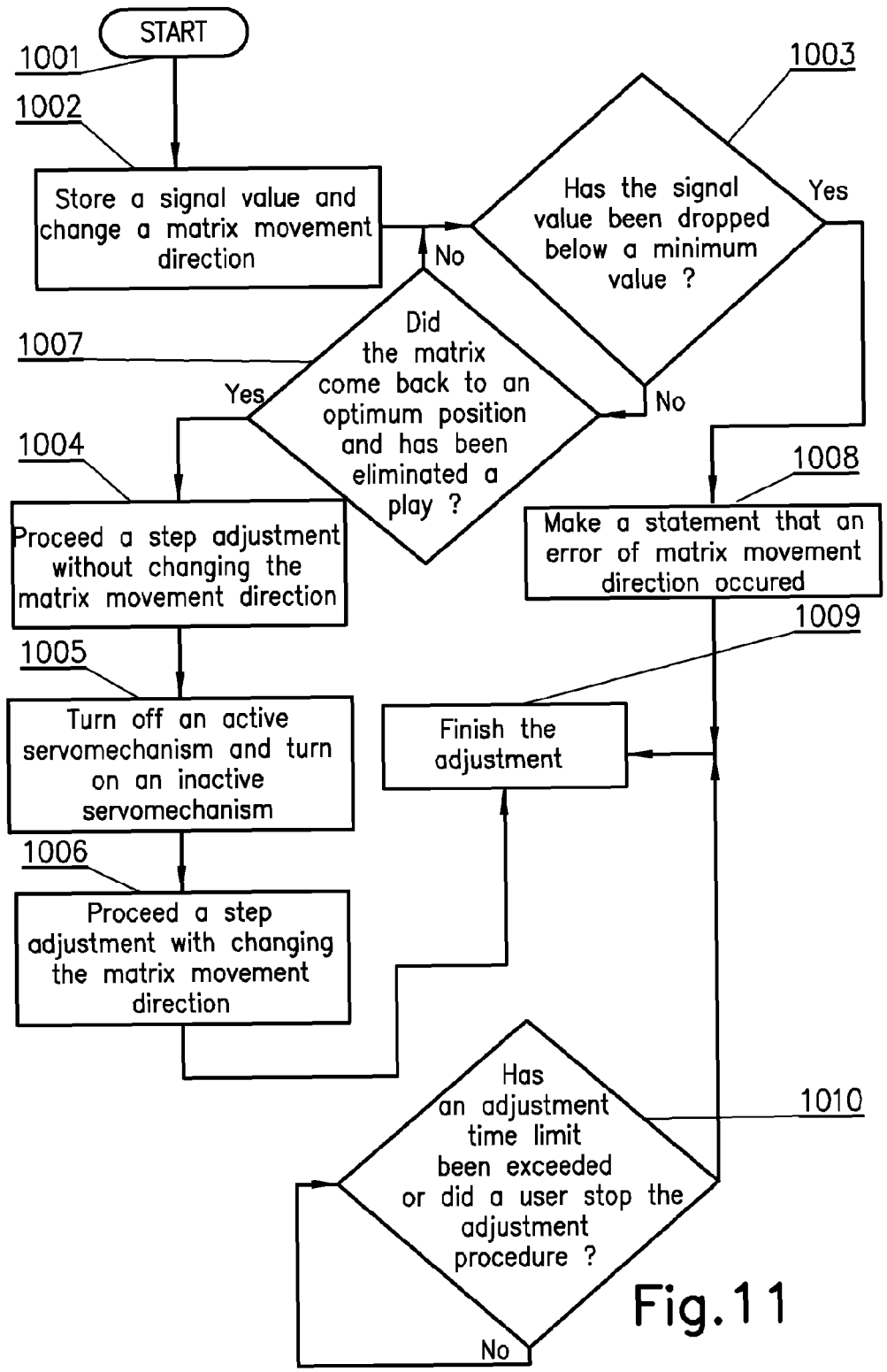
FIG. 11 shows a flow diagram of an adjusting finish procedure by applying one servomechanism.

FIG. 11 shows a flow diagram of the final adjustment using one of servomechanisms, also called a final adjustment with one parameter, which starts in step 1001, when the fine adjustment has been finished. In step 1002, a signal value is stored and a matrix movement direction is changed-over. In step 1003 it is checked if the signal drops below a minimum limit value, for instance below three hundred of units of account, and in step 1007, if the matrix comes back to an optimum position and a play or running clearance has been eliminated. When the matrix nearly reaches the optimum position, the input value or the average value of the electric signal generated by the detection device is stored in step 1004 and a step adjustment procedure is started. In step 1005 the active servomechanism is turn off and the inactive servomechanism is turn on to proceed the step adjustment with changing the matrix movement direction in step 1006, after which the adjustment procedure is finished in step 1009. When the signal drops below the minimum limit value, in step 1008 it is stated that an error occurred in respect to the matrix movement direction. The adjustment is finished in step 1009. The user can stop the procedure at any time, and if the user decides to finish the procedure, the procedure is broken by the user in step 1010. The procedure is also finished when the adjustment time limit has passed. The adjustment time is measured in step 1010.

Figure 12:
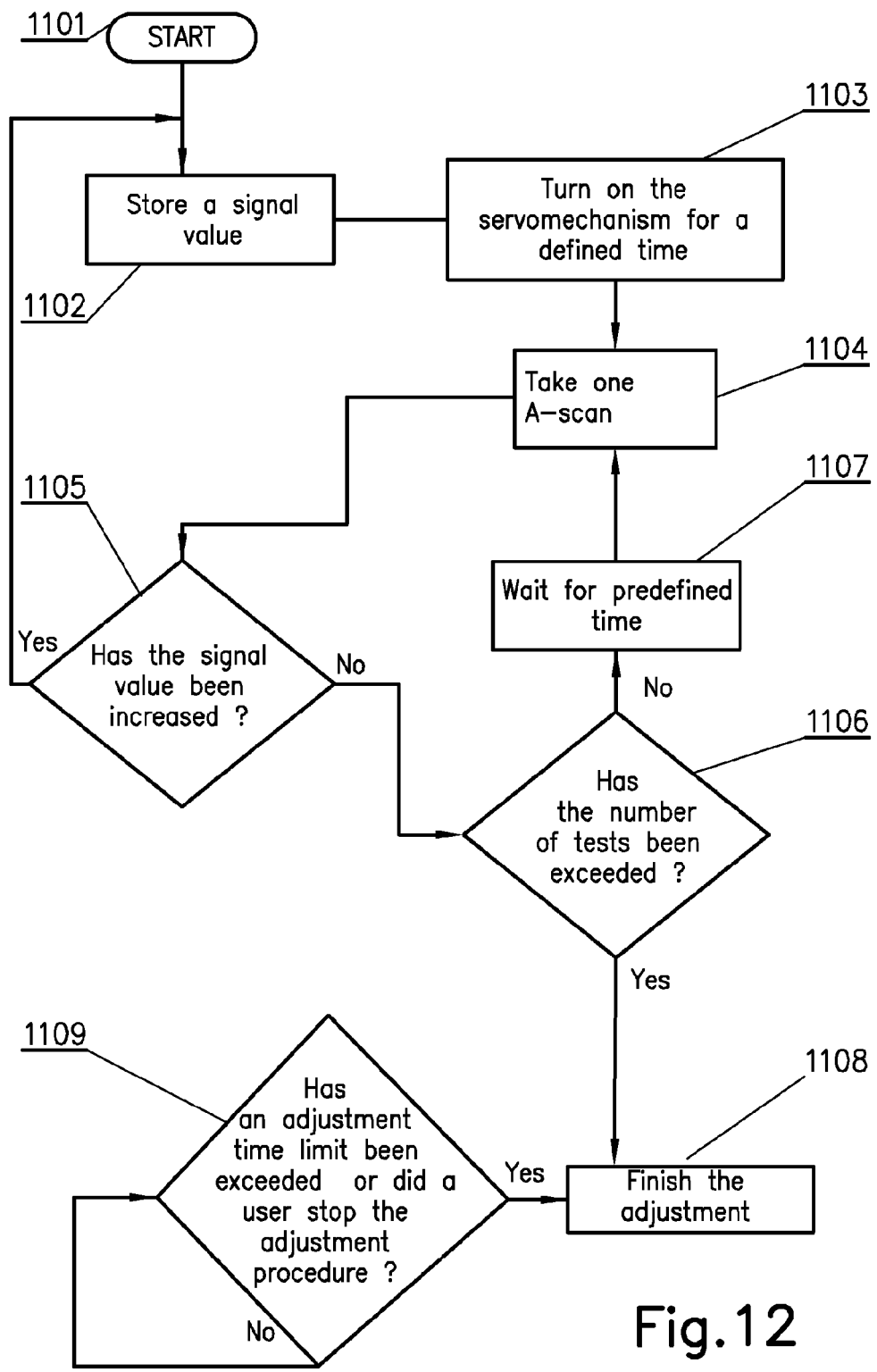
FIG. 12 shows a flow diagram of an adjusting step procedure.

FIG. 12 shows a flow diagram of the step adjustment, which starts in step 1101. In step 1102, a signal value is stored and the servomechanism is turn on for short time, for example for 300 ms, in step 1103. Next, the servomechanism is turn off and the value of the electric signal is measured after taking one A-scan in step 1104. In step 1105 it is checked whether the value of the electric signal has increased, and if yes, the adjustment is continued in step 1102. If the value of the electric signal did not increase, then in case when the number of tests set previously has been exceeded that is checked in step 1106, for example after taking twenty A-scans, the step adjustment is finished in step 1108. When the number of tests set previously has been not exceeded, then when passes a period of time previously set, for example 30 ms, measured in step 1107, the procedure is continued in step 1104 and a next A-scan is taken. The user can stop the procedure at any time, and if the user decides to finish the procedure, the procedure is broken by the user. The procedure is also finished when the adjustment time limit has passed. The adjustment time is measured in step 1109.

Figure 13:
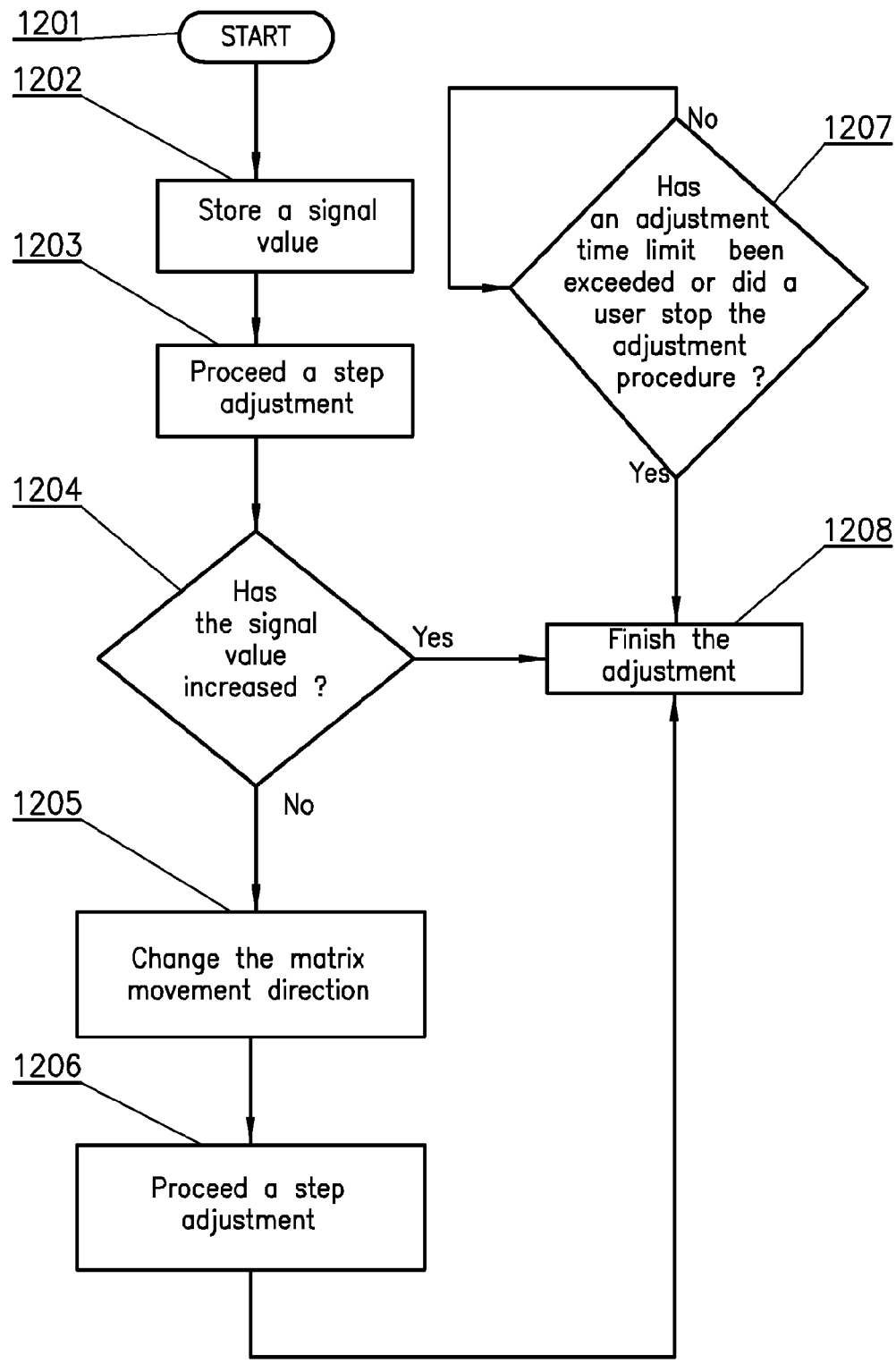
FIG. 13 shows a flow diagram of an adjusting step procedure with a change of matrix movement direction.

FIG. 13 shows a flow diagram of a step adjustment with changing-over direction of matrix rotation or movement, which starts in step 1201. In step 1202, a signal value is stored and then, in step 1203, the step adjustment, shown in FIG. 12, is proceeded. In step 1204 it is checked whether the value of the electric signal has increased and if no, then in step 1205, direction of rotation of the matrix is changed-over and the step adjustment, shown in FIG. 12, is proceeded. After the step adjustment, the step adjustment with changing-over direction of rotation is finished. The user can stop the step adjustment procedure at any time, and if the user decides to finish the step adjustment procedure, the step adjustment procedure is broken by the user in step 1208. The step adjustment procedure is also finished when the adjustment time limit has passed. The adjustment time is measured in step 1207.

Figure 14:
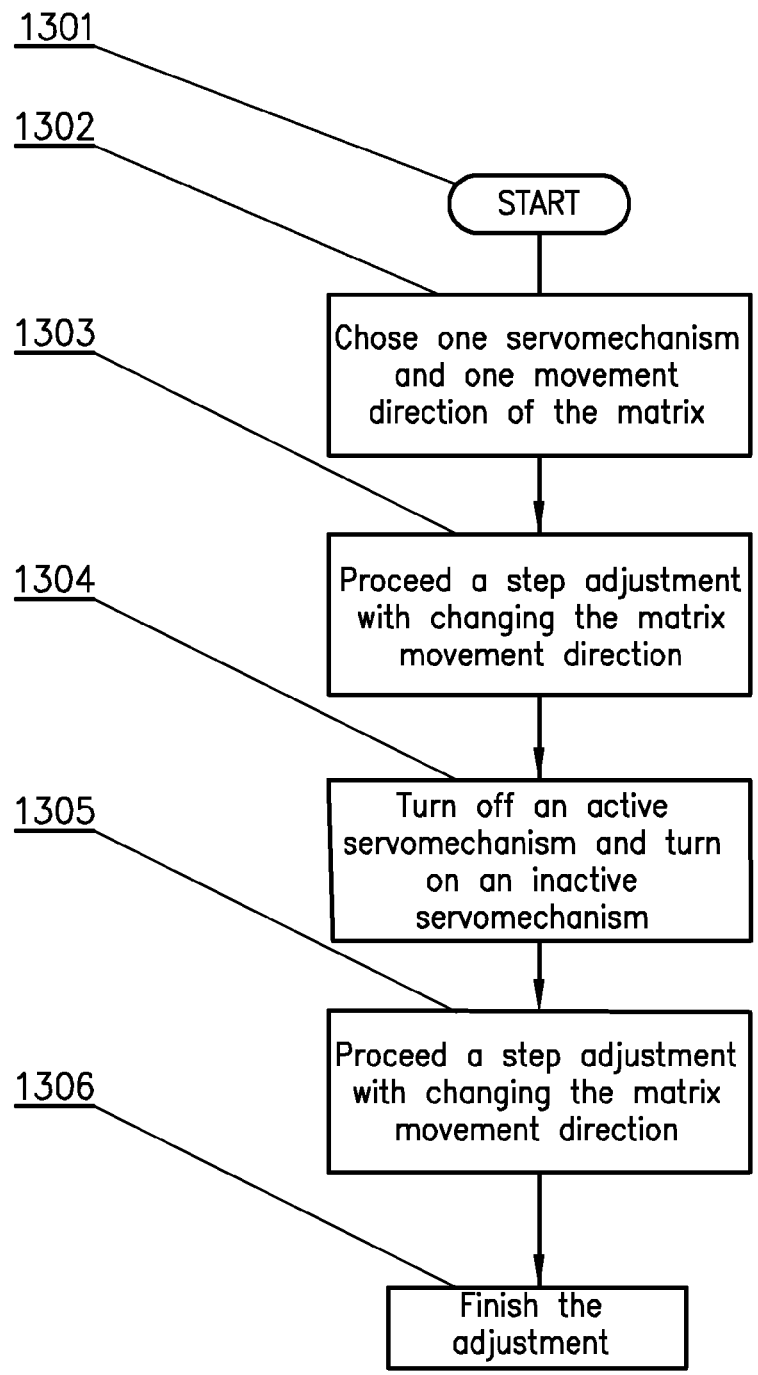
FIG. 14 shows a flow diagram of an adjusting step procedure with a change of servomechanism.

FIG. 14 shows a flow diagram of the step adjustment with changing of the servomechanism, which starts in step 1301. In step 1302, one of servomechanisms and one direction of the matrix movement are chosen, after which the step adjustment with changing-over matrix direction of rotation is proceeded in step 1303. In step 1304 is turn off an active servomechanism and turn on an inactive servomechanism, and next, in step 1305, the step adjustment with changing-over matrix direction of rotation is proceeded. The step adjustment with changing of the servomechanism is finished in step 1306.

After finishing the adjustment procedure of the apparatus for optical frequency domain tomography, this late can be used for examining the objects, which is based on a method of signal measurement by applying the optical frequency comb, which in turn, is based on multiple (or in certain circumstances single) registration of the optical frequency comb with simultaneous changes of its components position. For displaying a complete cross-section of the object, the object light beam must be moved along the object in a direction perpendicular to the direction of the object beam propagation and for every position of the object beam a signal must be registered and converted into data, which after processing enables the creation of the complete cross-sectional image.

It is essential that the optical frequency comb, consisting of discrete, equidistant, narrowly separated, spectral components may be set up in two ways, namely, either by using a broadband light source and frequency modes as a discriminatory tool or using optical frequency comb generators based on phase modulation and an additional reflective cavity. In the first arrangement it is possible to separate light of different wave-lengths by using interference phenomena as per the Fabry-Perot experiment. In the second case the generation of the optical frequency comb is based on high-power electro-optic modulators, which can impose dozens of sidebands on a single-frequency input beam from a single-frequency continuous-wave laser. It is also known that this process can be made more efficient by placing the modulator in a resonant cavity, particularly when intracavity dispersion has been reduced to a minimum. Either method of optical frequency comb generation can be used in the described invention.

Figure 30:
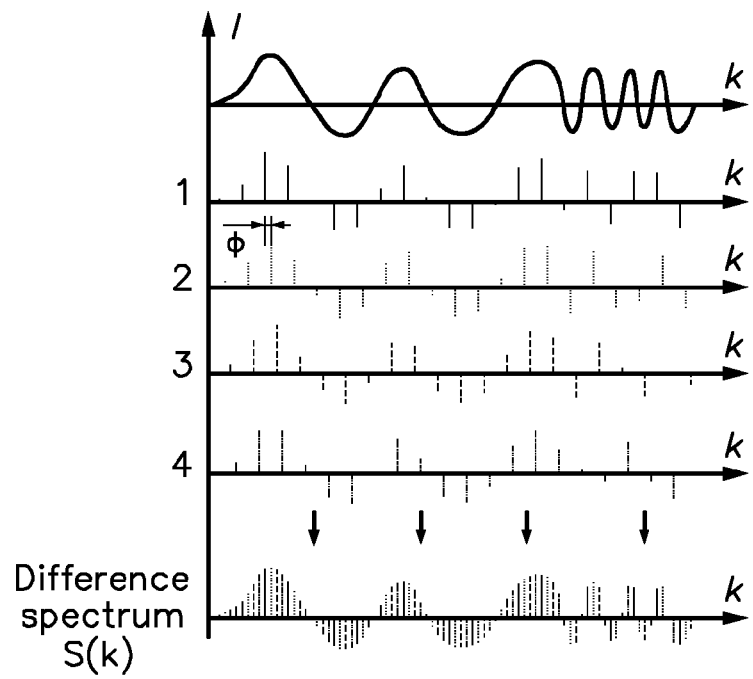
FIG. 30 shows a method of multiplexing spectra into a resultant multiple spectrum.

Also an essential component of this invention is possibility to adjust and control a position of the whole comb in the optical frequency domain. FIGS. 17 and 18 show the idea of shifting the entire comb on the λ axis by an increment of φ, shown in FIG. 30, and multiplexing the resultant spectrum signals. The optical frequency comb can be moved, for example, by using the tuned Fabry-Perot interferometer, in which the distance between the interferometer mirrors is variable. In this case changes of the distance d between the reflecting planes in the tuned Fabry-Perot interferometer influence the value of φ of the movement of the optical frequency comb and the distance FSR between neighbouring optical components $\lambda_s$ of the optical frequency comb or the set of components. However the difference between $FSR_1$ for the distance $d_1$ between the reflecting planes of the tuned Fabry-Perot interferometer and $FSR_2$ for distance $d_2$ is neglected because it is much lower than the value of the complete shift by the value of φ of the optical frequency comb. The value of the position alteration φ of the optical frequency comb can be random, but must be known, because it is used during the digital data processing.

The steps of the methods described bellow do not necessarily need to be performed serially and may be performed simultaneously.

Figure 19:
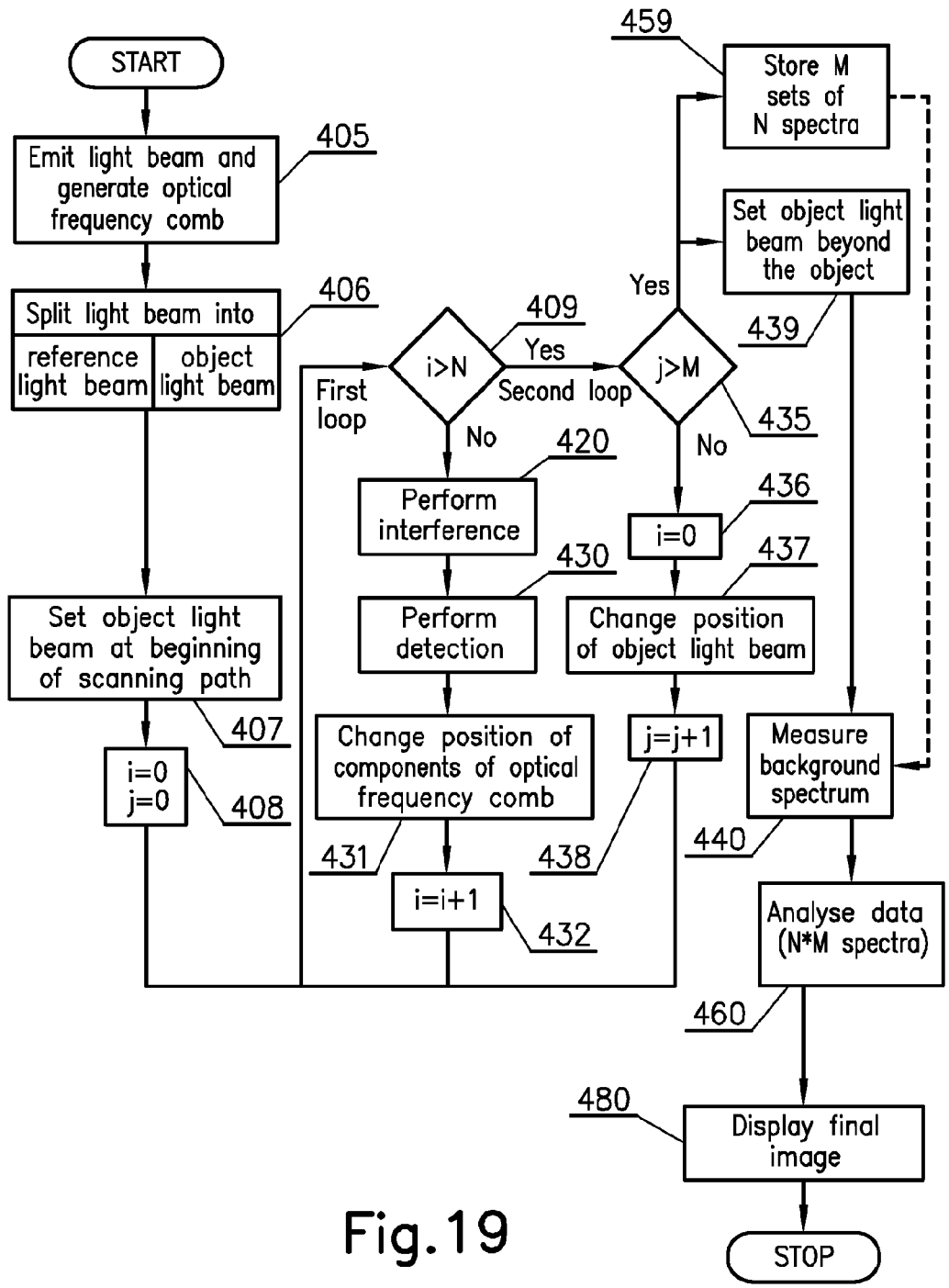
FIG. 19 shows a flow chart of a method for imaging of objects using optical frequency domain tomography.

The method for imaging of objects using optical frequency domain tomography is shown in FIG. 19. First, in step 405, the light beam is generated and the optical frequency comb is formed. Then, in step 406 the light beam is split into the reference light beam and the object light beam and in step 407 the object light beam is set to initiate the scanning path. It is possible that the optical frequency comb is formed in the reference light beam and the object light beam after splitting the light beam generated by the light source. In step 408 i and j are set to zero and in step 409 i and N are compared if i is bigger than N. If i is lower than N or equal to N, interference, shown in FIG. 20, consisting of steps 415-418, is performed in step 420. In step 430 the spectrum is identified. The spectrum is detected and registered by the multi-element photodetector or the detection device in such a way that one discrete photosensitive element of the detection device detects and registers not more than one component of the optical frequency comb. The detection and registration of the spectrum is described in detail in the text with reference to FIGS. 27-29. Next, in step 431 the position of the mirrors of the tuned Fabry-Perot interferometer is set thereby the positions of the components of the optical frequency comb are changed by the predefined and known value $\phi$. In step 432 i is increased by 1. Steps 420-431 form the first loop and are repeated N times. The optimum number of repetitions N is equal to the value of ratio FSR to $\phi$, and the method for changing the positions of the optical frequency comb is presented in FIG. 30. Changes of optical frequency comb positions are caused by the electric signal 181, as presented in FIG. 31 synchronized with electric signals 182, 184. If the value of the ratio FSR to $\phi$ is not an integer, the shift distance/value $\phi$ must be modified in such a way as to make N=FSR/$\phi$ a whole number. In step 435 it is checked whether j is higher than M. If j is lower than M or equal to M, i is set to zero in step 436, the position of the object light beam is changed in step 437 and in step 438, j is increased by 1 and the procedure is moved to step 409. Steps 409-438 form the second loop and are repeated M times. In this loop a number of iteration M means a number of lines of the resulting cross-sectional image of the object being examined and depends on the purpose of the examination. When the object light beam reaches the end of the scanning path, M sets consisting of N spectra is registered. Then, the procedure is moved to step 439, in which the object light beam is moved beyond the object or is blanked off or is turned-off. In step 440 a background spectrum is determined and data analysis of M sets consisting of N spectra is performed in step 460. The data analysis is shown in details in FIG. 24 and in FIG. 25. Then, the procedure is continued in step 480, in which all calculated lines called A-scans are displayed side by side, a final result being a cross-section or a three dimensional representation of the object, depending whether scanning of the object by the object light beam was in one, or in two axes perpendicularly to the direction of light propagation in the object light beam.

In an embodiment, in which the reference mirror is coupled to the positioning device 131 capable of moving the reference mirror by a distance equal to a light wave length, there is a possibility to perform an additional measurement for each position of the object light beam by changing the position of the reference mirror by a distance equal to a fraction of the optical wave length. This allows several A-scans to be taken at the same position of the object light beam and due to this it is possible to determine a phase as well as an amplitude of the interference signal as in the Complex Spectral OCT method.

Figure 20:
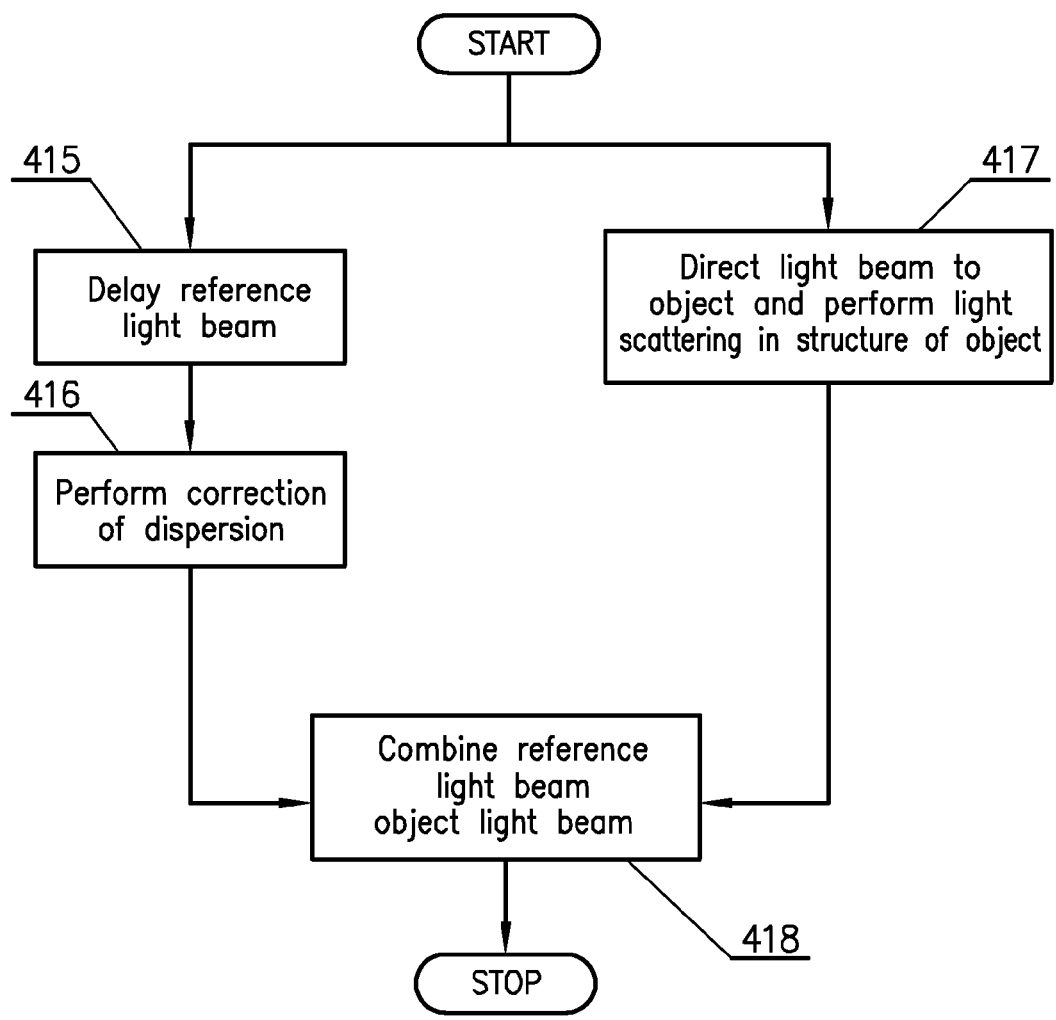
FIG. 20 shows a flow chart of interference.

FIG. 20 illustrates the interference of at least one object light beam and at least one reference light beam, in the shape of the optical frequency comb with an envelope surrounding the maxima of light intensity at particular component wave lengths, which has a form corresponding to the shape of the spectrum of the light beam generated by the light source. The interference, presented in FIG. 19 as step 420, begins by forming the reference light beam and the object light beam after splitting the light beam generated by the light source. In step 415 one of the light beams, modified to have a shape of the optical frequency comb, is delayed to equalise a travel time of the reference light beam moving along a reference light beam path and a travel time of the object light beam moving along an object light beam path that extends to the first selected layer of the object being examined. Then, in step 416 the dispersion is corrected and in step 417 at least one of the light beams is directed onto the object and focused on it. Next, in step 418, the object light beam, scattered off and reflected from the internal structures of the object, is combined with the reference light beam to form a resultant light beam, in which the individual components of the optical frequency comb of the reference light beam interfere with the respective components of the optical frequency comb of the object light beam returning from the object.

Figure 21:
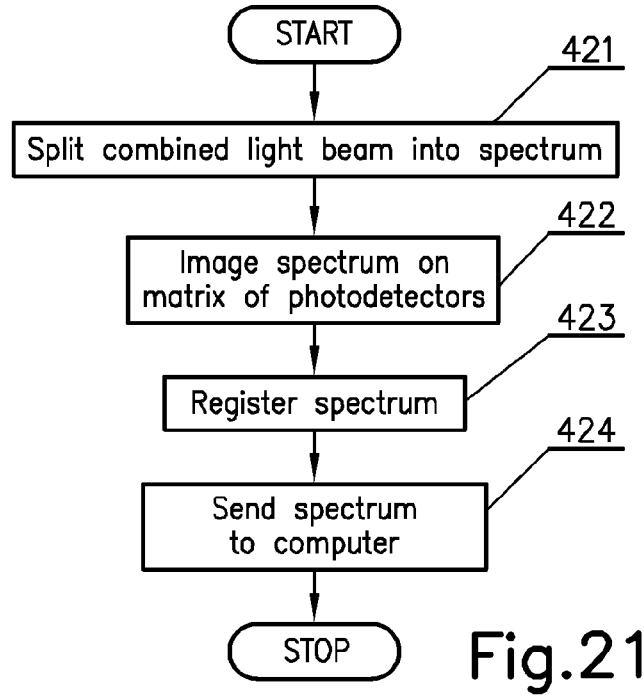
FIG. 21 shows a flow chart of an algorithm for detecting of a spectrum.

FIG. 21 shows one of embodiments of an algorithm for detecting of the spectrum. First, in step 421 the components of the optical frequency comb of the resultant light beam, formed from components of the optical frequency comb of the reference light beam and components of the optical frequency comb of the object light beam, are split spatially to form a resultant spectrum, which is projected onto the multi-element photo-detector or the photosensitive elements of the detection device in step 422. In step 423 the resultant spectrum is registered by the photo-detector in such a way that one discrete photosensitive element of the multi-element photo-detector registers not more than one component of the optical frequency comb of the resultant spectrum. In other embodiment, the design of the system is such that one discrete photosensitive element of the multi-element photo-detector detects and registers only a part of one component of the optical frequency comb of the resultant light beam and that means that one component of the optical frequency comb of the resultant light beam is detected and registered by few discrete photosensitive elements.

An electrical signal is generated in the discrete photosensitive element of the multi-element photo-detector. This signal corresponds to the light intensity resulting from the interference of a particular component of the optical frequency comb of the reference light beam and its corresponding component of the optical frequency comb of the object light beam returning from the object what means that only components of the same ranges of wave length can interfere with each other. At least, in step 424 the electrical signal generated in the multi-element photo-detector is digitised and transferred to the processing arrangement, for example a calculation unit.

Figure 27:
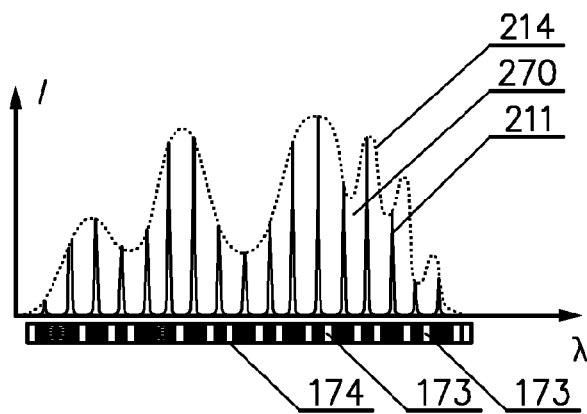
FIGS. 27-29 show methods of imaging of spectrum onto a matrix of a detection device.

It is possible to perform the spectrum detection in several ways. The first possibility, as presented in FIG. 27, is such, that the components of the optical frequency comb fall upon the multi-element photo-detector, for example the matrix 174 of photosensitive elements in a free way, but in such a way, that a single cell or a single pixel or a single photosensitive element registers not more than one component. The advantage of such a configuration is that no digital calculation of spectra between wavelength $\lambda$ and wavenumber k is required. Choice is only made of interpolated points from every registered spectrum in a way described from step 442 to 455 of the algorithm presented in FIG. 23. The process of interpolating the choice of points is about 70% less time-consuming than the currently-applied method for the digital calculation of spectra from $\lambda$ to k by using an analytical formula. Another advantage of this configuration is to minimise the effect of averaging the interference fringes after sectioning the wavelengths registered by a single pixel of the matrix of photosensitive elements. This is possible because the single pixel of the matrix receives an approximately monochromatic wave, this being an effect of using the optical frequency comb as a light source in a device for spectral optical tomography operated at optical frequencies. In such a configuration it is also possible to make measurements of N spectra that are combined into a single resultant compound spectrum as described. Thanks to this, the range of imaging can be increased N-times without losing the resolution of the axial method.

Figure 28:
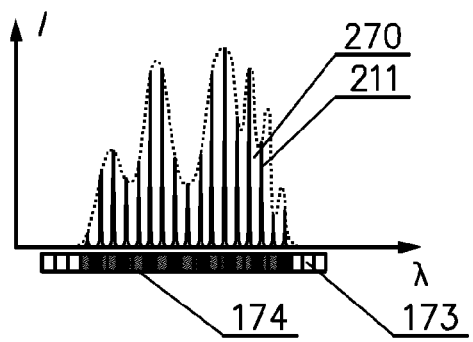
Figure 29:
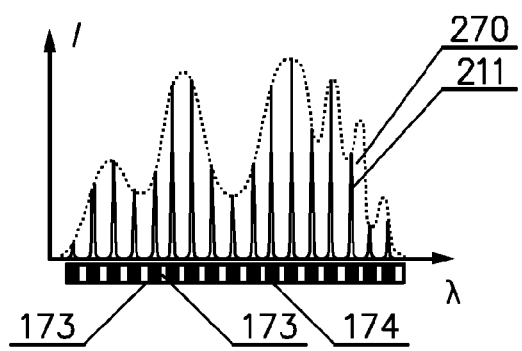

A second possible configuration of a method for spectrum detection is presented in FIG. 28. Due to the fact that the change of the distance between the components of the optical frequency comb (if they are registered in domain $\lambda$) simultaneously with moderate wavelength increase, it is possible to design the spectrometer in such a way that the individual components of the optical frequency comb fall exactly into the individual pixels on the matrix of photosensitive elements or individual photosensitive elements of the detection device.

In such a configuration step 445 is not required, this being the step in which the positions of individual components in the matrix of photosensitive elements are set, because they are known if the spectrometer has been properly designed. This information is used in step 455 of the algorithm presented in FIG. 23, in which an appropriate choice of points of a registered spectrum is made so as to create a spectrum in domain k. This method of spectrum detection eliminates the need for interpolation of spectrum values and at the same time allows a further increase in the speed of numerical processing of registered data.

Figure 22:
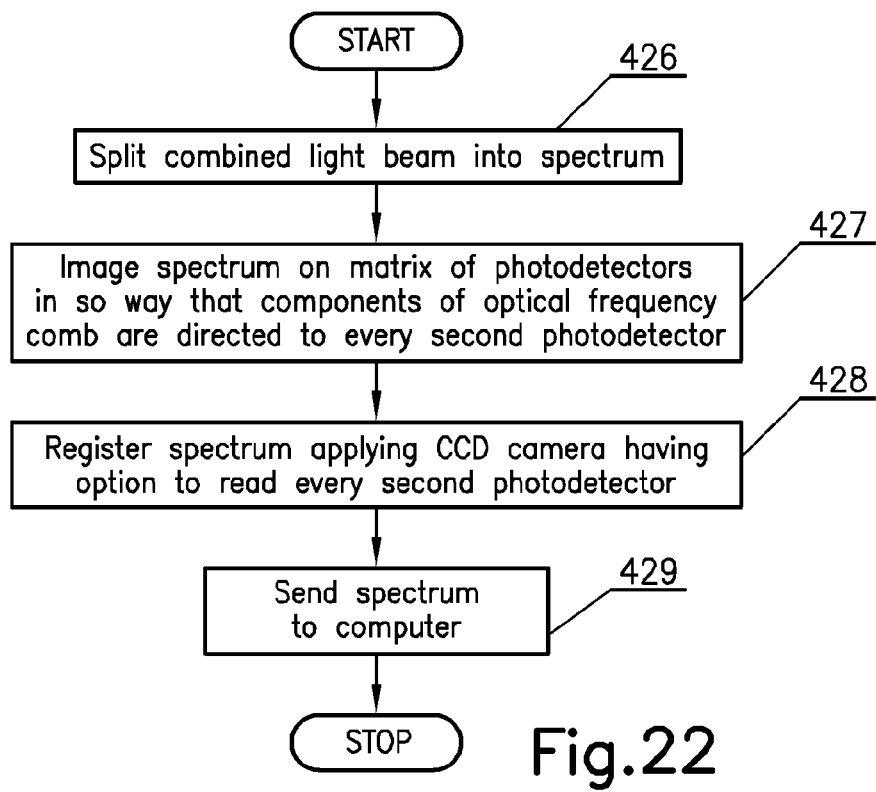
FIG. 22 shows a flow chart of further variant of an algorithm for detecting of a spectrum.

FIG. 22 presents another variant of spectrum detection, shown in FIG. 19 as step 430, which starts from creating the resultant spectrum from the object light beam and the reference light beam in step 426. In step 427 the resultant spectrum is formed in such a way that the components of the optical frequency comb fall upon every second photosensitive element of the matrix of photosensitive elements or every second photosensitive element of the detection device. Next, in step 428, the resultant spectrum is registered by using a CCD device option for reading every second pixel or photosensitive element, and electrical signals generated by the photosensitive elements of the detection device are transmitted to the calculation unit in step 429. This variant of spectrum detection has all the advantages of the two earlier configurations, and also significantly reduces the decrease of spectrometer resolution caused by charge leakage in the matrix of photosensitive elements in the form of CCD devices. In this configuration the spectrometer is designed in such a way that the individual components of optical frequency comb 211 fall into every second photosensitive element of the matrix 173 of photosensitive elements, which is shown in detail in FIG. 29. Thanks to such a solution any charge-leakage from lighted photosensitive elements moves to neighbouring photosensitive elements which hold no usable signals, and thus there is no decrease in the detector's spectral resolution and no decreasing signal in the form of the amplitude of the interference fringes modulating the optical frequency comb. Reading the spectrum in this configuration can be done in two ways: either by reading all photosensitive elements and selecting every second point from the collected data, or by using an option available in industrial CCD devices for reading only every q-th pixel or every q-th photosensitive element at each the component is registered, for example odd or even uneven pixels or photosensitive elements. This way doubles the reading-rate of spectra and simultaneously a spectrum directly positioned in domain k is created.

Alignment of the distances between the components of the component set and their correlation with the distances between the pixels or photosensitive elements in the detection device may be achieved in many ways. One way is to arrange the inter-mirror distances of the Fabry-Perot interferometer or the adjustable or tuned Fabry-Perot interferometer in such a way that every component of the resultant spectrum, this being the set or group of component modulated by the interference signal falls into every q-th pixel or photosensitive element of the detection device that means these distances must correspond with the photosensitive elements of the detection device, in which case q must be greater than 0.

In the second method angles between the resultant light beam and the device separating spatially wavelength components are set to specific value so that the components of the resultant beam, forming the set or group of components modified by the interference signal such that again, they correspond to the photosensitive elements of the detection device and every component of the resultant spectrum reaches every q-th pixel or photosensitive element of the detection device, in which case q must be greater than 0.

Another method concerns the case where the angle of the resultant light beam directed towards the detection device in such a way that the angle of incidence of the resultant light beam on the device separating spatially wavelength components is adjusted such that the individual components of the resultant spectrum of the resultant light beam are matched to every q-th photosensitive element of the detection device, where q>0.

Figure 23:
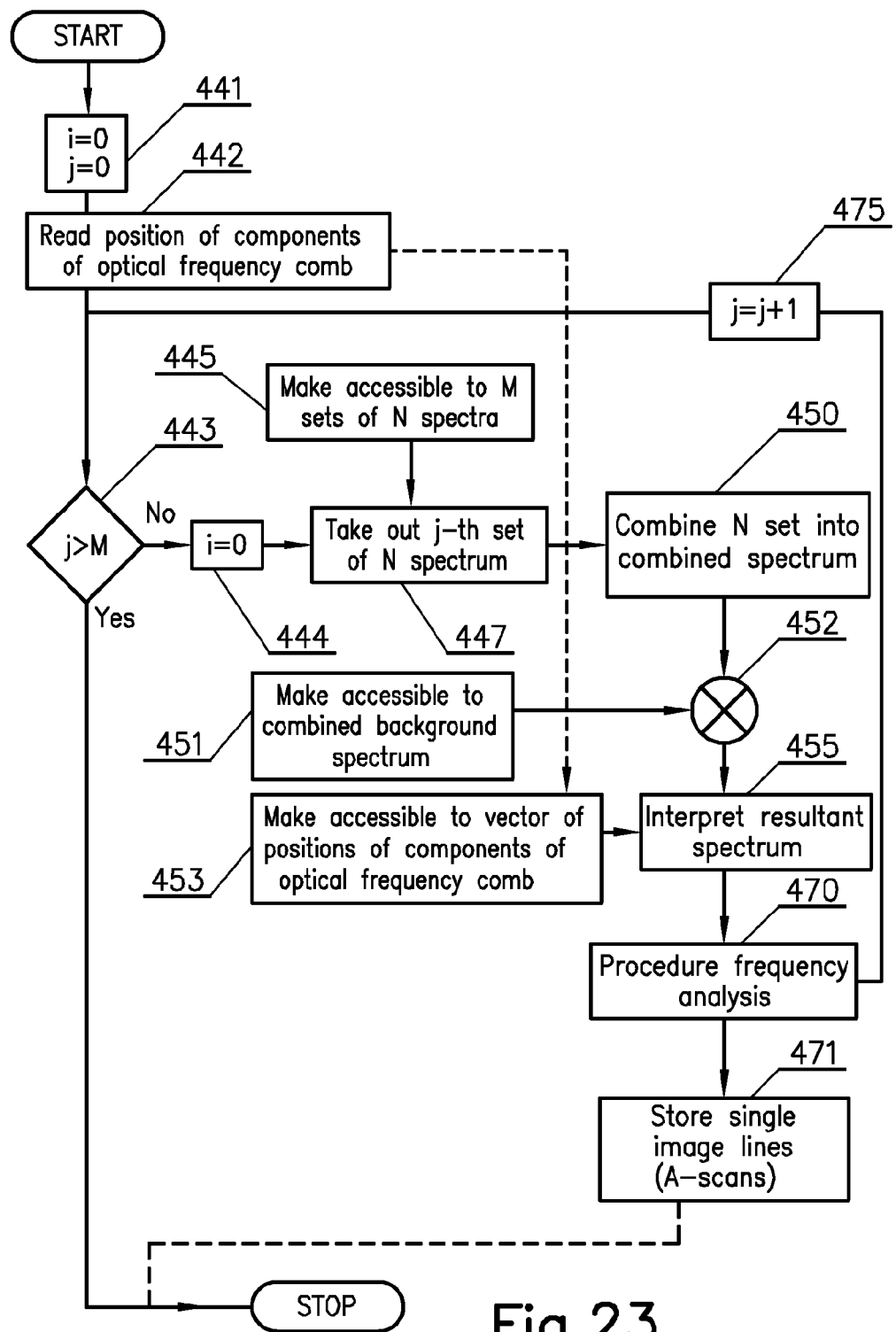
FIG. 23 shows a flow chart of the first variant of data analysis.
Figure 32:
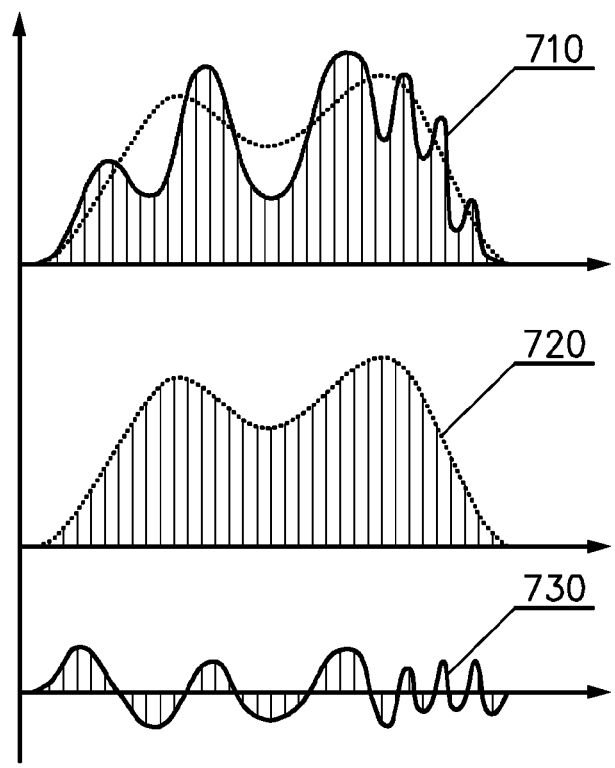
FIG. 32 shows a way to form a difference spectrum.

FIG. 23 presents one variant of data analysis, which begins in step 441 with zero setting of i and j. In step 442 a calculation unit reads positions of optical frequency comb components from a resultant compound spectrum assembled in a multiplex way in step 460. The result of this operation is a vector of component positions. In step 443 it is checked if j is higher than M. If j is lower than M, then in step 444, i is set to zero and in step 447 another set of N spectra is selected from the registered M sets made available in step 445. In step 450, N spectra of a given set are combined into one spectrum consisting of spectra made available in step 451. In step 452, the background spectrum is subtracted from the combined multiple spectrum, as described in FIG. 32. In step 455 the resultant multi spectrum is decoded such that only those points are chosen from the resultant multi spectrum, which correspond to values from the vector position of components selected in step 445 and made available in step 453. The decoded resultant multi spectrum is then received directly in wavenumber domain k. In step 470 the decoded resultant multi spectrum is analysed in terms of frequency, for instance, by applying the Fourier transformation, producing a single line—called an A-scan—of a cross-sectional image of examined object, which is recorded in the calculation unit in step 471. If it is not the last A-scan, then in step 475 j is increased by 1. Analysis of data can be made after completing the second loop of recording and collecting data in steps 460 or 560 of the algorithms shown in FIGS. 19 and 24, but the process may occur both inside the first or the second loop.

Figure 24:
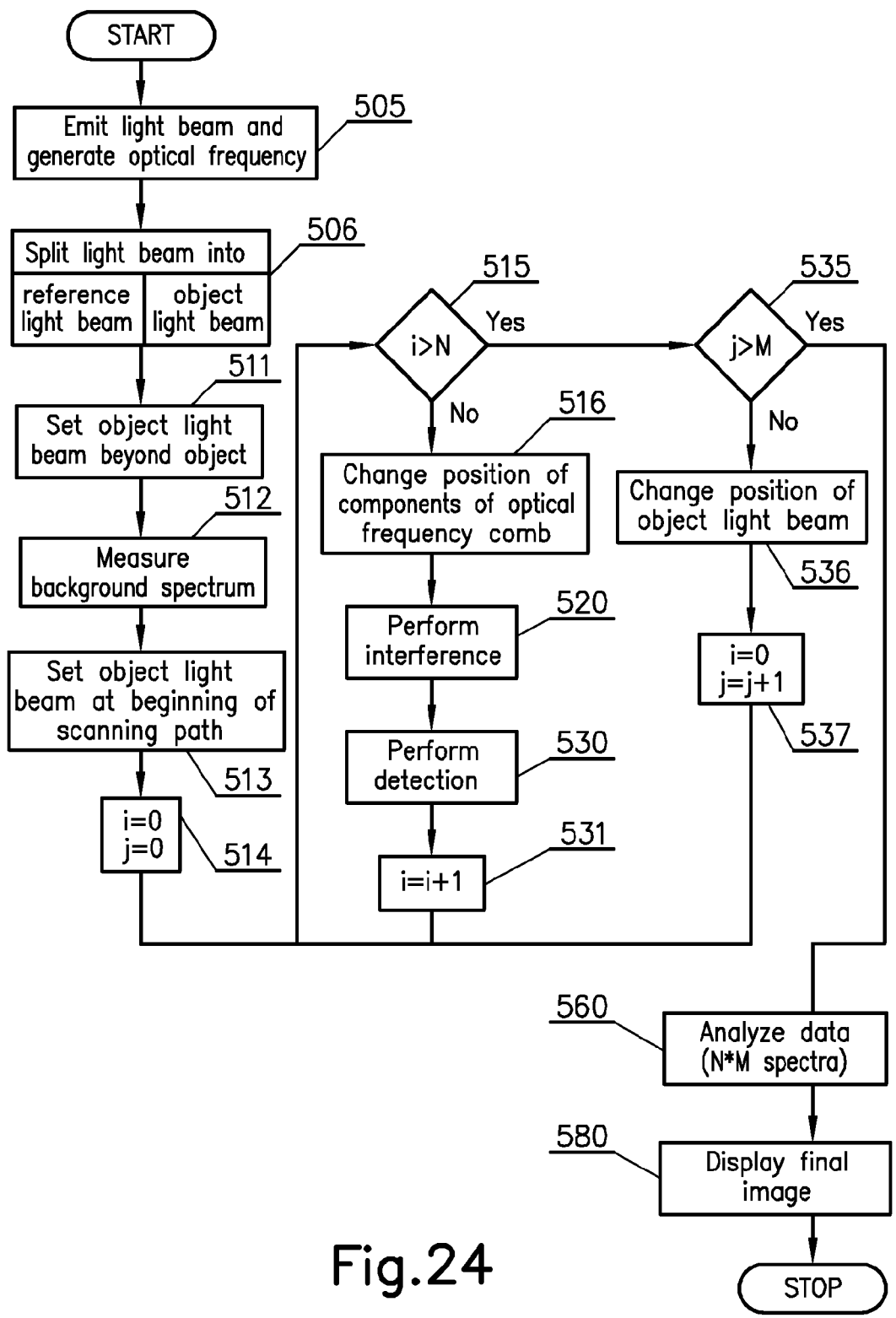
FIG. 24 shows a flow chart of further variant of a method for imaging of objects using optical frequency domain tomography.

FIG. 24 shows another algorithm for imaging objects. The procedure begins by generating the light beam and forming the optical frequency comb in step 505 and dividing the light beam into a reference light beam and an object light beam in step 506 and establishing what will be referred to as a background spectrum by directing the object beam outside the object in step 511. In step 512 recording is made of the background spectrum. In step 513 the object light beam is set at the beginning of the scanning path whilst in step 514 i and j are set to zero. In step 515 it is checked if i is higher than N. If i is equal to or lower than N, changes of positions of the optical frequency comb components take place in step 516, after which in step 520 interference of object and reference beams occurs, as described in steps 415-418. In step 530 detection of the resultant spectrum of the resultant light beam is made and it is transferred into an electrical signal, which is performed as described in reference to step 430. Next, i is increased by 1 and the procedure is continued in step 515. When the light beam reaches its final position of the scanning path, then in step 535 it is checked whether j is equal to M, which would signify that the whole object has been scanned. If j is lower than M, the procedure is continued in step 536, in which a change of the position of the object light beam takes place, after which i is reset to zero, and j is increased by 1 in step 537 and the procedure is moved to step 515. After scanning the entire object, data analysis is made in step 560, and in step 580 all calculated A-scans are displayed side by side, and the final result is a cross-section or a three dimensional representation of the examined object, depending whether scanning by the object beam was made in one or in two axes perpendicular to the trajectory of the object beam.

Figure 25:
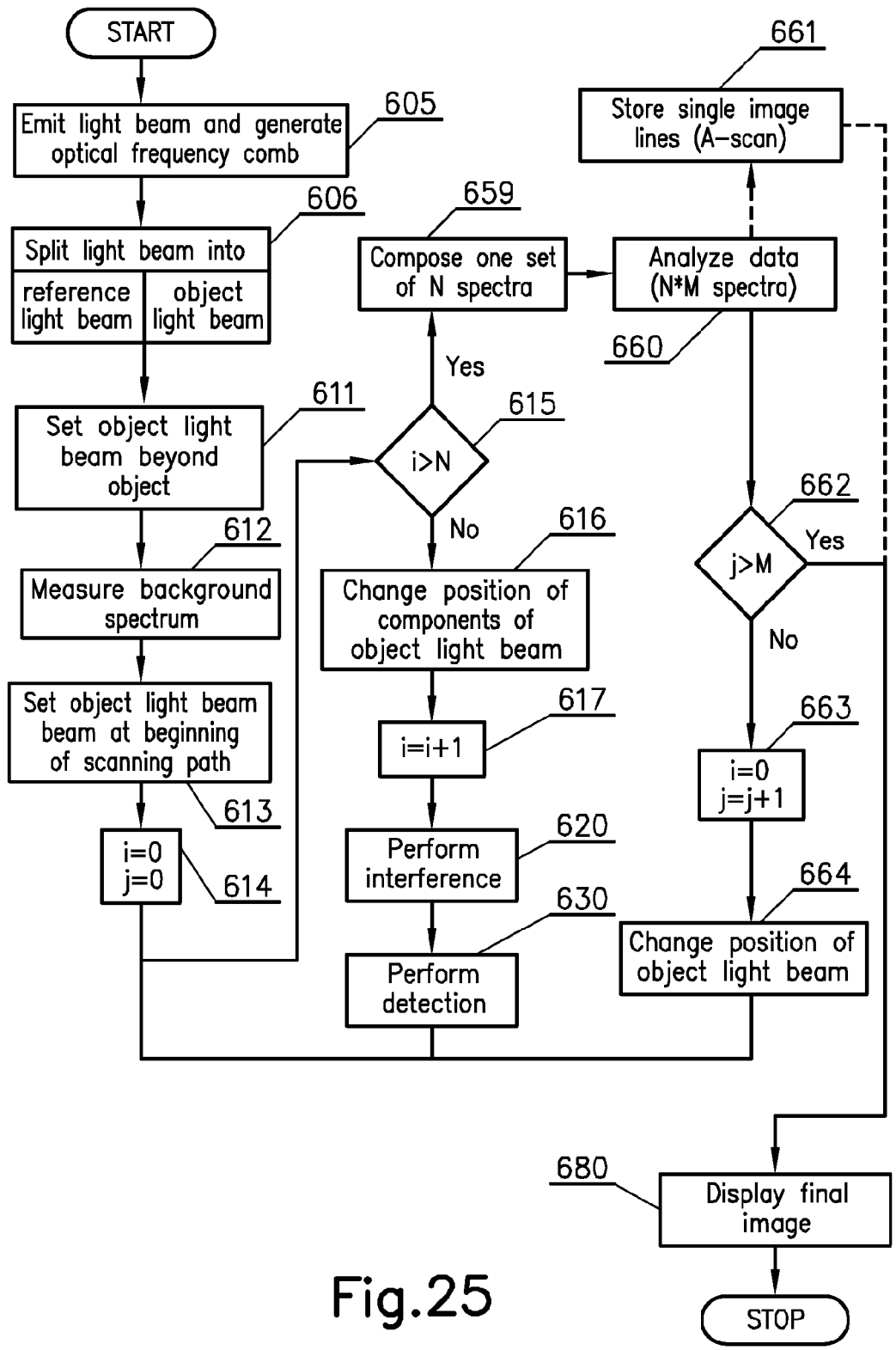
FIG. 25 shows a flow chart of yet further variant of a method for imaging of objects using optical frequency domain tomography.

FIG. 25 shows yet another algorithm for imaging objects. As in previous variants of object imaging algorithms, a procedure begins from the generation of a light beam and forming of the optical frequency comb, which is carried out in step 605, beam-splitting into reference and object beams in step 606 and setting the object light beam beyond the object in step 611. In step 612 background measurement is made, and in step 613 the object light beam is set at the beginning of its scanning path. In step 614 i and j are reset to zero. In step 615 it is checked if i is higher than N. If i is lower than N, a change of the position of the optical frequency comb components takes place in step 616, after which, in step 620, interference of the object and reference beams occurs, as described in steps 415-418. In step 630 the spectrum is detected. If it turns out after checking in step 615, that i is higher, in step 659 one set of N spectra is registered, and in step 660 data analysis is made regarding N spectra, which includes subtracting background spectrum from every one of registered N spectra, decoding spectra by using vector of components' positions receiving partial spectra, assembly of partial spectra into a compound spectrum, making frequency analysis and as a result of which one line is received, so called one A-scan. Decoding the spectrum involves the use of the vectors of component positions to yield sub-spectra, combining these into a resultant spectrum, performing frequency analysis to obtain a one-line A-scan which provides information about a discrete linear part of the image aligned with the object light beam and which has its width and a length equal to that of the object being examined. If the object light beam has a circular cross-section the part of the object being scanned forms a cylinder and when the beam is formed with a linear cross-section the obtained image corresponds to a cubicoidal fragment of the examined object. In step 661 single lines of an image are collected. In step 662 it is checked whether j is higher than M, and in case when j is lower than M, then in step 663 i is reset to zero, and j is increased by 1 and the procedure is continued in step 615, repeating mentioned steps M times, as a result getting a ready image consisting of M lines, which is displayed in step 680.

Figure 26:
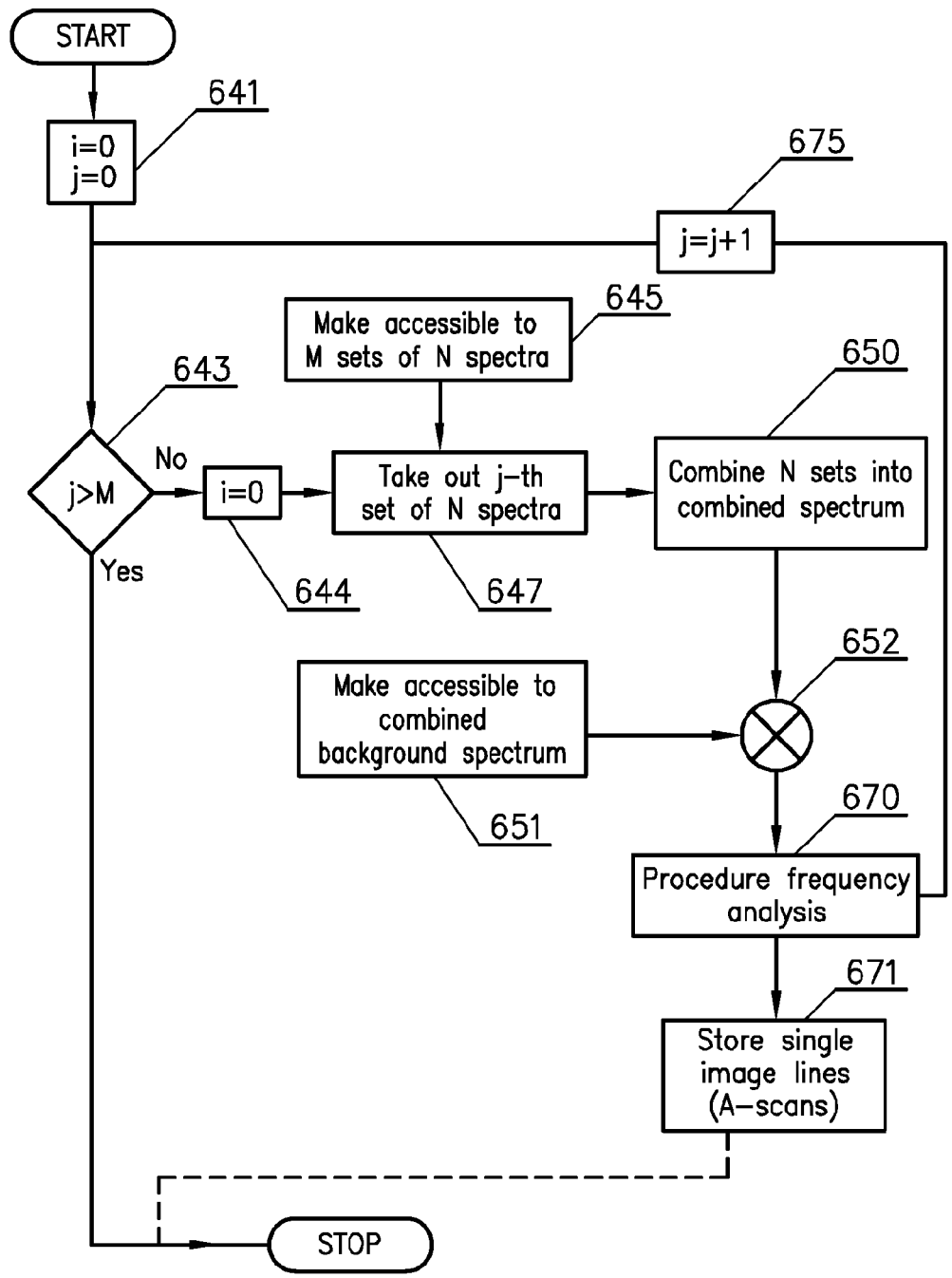
FIG. 26 shows a flow chart of another variant of data analysis.
Figure 33:
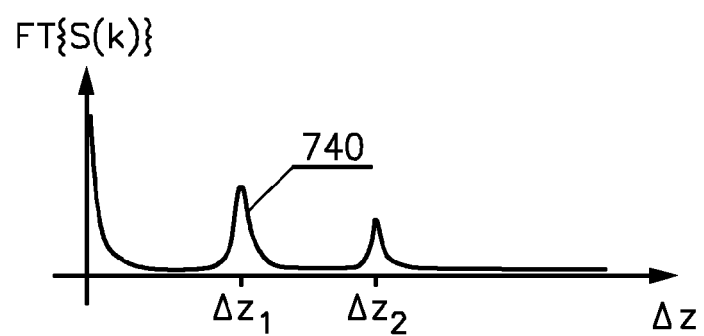
FIG. 33 shows the Fourier transformation of an individual line of an object cross-section.

FIG. 26 presents another variant of data analysis, which is used in the algorithm shown in FIG. 25, and which begins in step 641 by setting to zero values i and j. In step 643 it is checked if j is higher than M. If j is lower than M, in step 644 i is reset to zero, and in step 647 another set of N spectra is chosen out of the registered M sets made accessible in step 645. In step 650, N spectra of a given set are assembled into one compound spectrum. In step 652 from compound spectrum, a compound spectrum of background made accessible in step 651 is subtracted, according to the way presented in FIG. 32, in which from the resultant spectrum 710 the background spectrum 720 is subtracted and a resultant compound spectrum 730 is received. In step 670 frequency analysis of resultant compound spectrum 730 is made, for example by calculating Fourier transformation, receiving an object single line 740 of cross-section image of examined object called A-scan, shown in FIG. 33. Peaks at distances $\Delta z_1$ and $\Delta z_2$ from a datum surface correspond to two back-scattering or reflecting points creating an axial structure of reconstructed object. The single object line is registered in step 671. If it is not the last A-scan, then in step 675 j is increased by 1.

In comparison with hitherto known methods of OCT imaging, the presented solution has numerous advantages. Thanks to this solution there is a significant reduction of limitations as known in the SOCT method, connected with averaging of the interference signal after sub-dividing the frequency band corresponding to photosensitive element width due to the fact, that single photosensitive elements register monochromatic radiation fairly accurately. Moreover, this solution eliminates the need for numerical calculation of the registered spectrum from domain of wave-lengths to optical frequencies due to the fact that components of quasi-discrete spectrum registered by spectrometer are equally spaced in the domain of optical frequencies. Thanks to this solution, the time of data processing has been reduced due to the significantly shorter operational time to interpolate the values of the recorded spectra in the positions set by the components of the optical frequency comb as compared with the numerical calculation of the spectra applied in currently known SOCT techniques. In case of a configuration in which the components fall into exactly positioned pixels of the matrix of photosensitive elements, the spectra are registered directly in the domain of the wavenumber k, and no additional numerical operations are required, which further shortens numerical data processing. The significant advantage of such a solution is an increase in spectrometer resolution by minimising the effect of charge leakage in the CCD detectors by such adjustment of distances between the components of the optical frequency comb so as to make the components fall exactly into a q-th cell or photosensitive element of the matrix of photosensitive elements, in a specific case onto every second photosensitive element. The effect of charge leakage in this method of detection still exists, but it does not influence the usable signal, because leaking charges from a given pixel move to neighbouring pixels, which are not used to construct the spectrum being recorded. It is true that in this way half of the photosensitive elements of the detector are unavailable (in the variant in which every second photosensitive element is illuminated), but the drawback can be easily averted by using a detection device with twice the density of photosensitive cells or elements. Furthermore, the limitations of the SSOCT system connected with mode hopping are eliminated when a light source and the Fabry-Perot interferometer of wide spectrum (low time coherence) is used to generate the optical frequency comb. This results in an effective increase of the imaging range achieved by increasing the effective number of interference fringes sampling signals in a process of multiple spectrum registration and assembling them into a spectrum consisting of higher number of points.

The presented apparatus and the method for imaging the interior structure of objects allow their complex measurement, in which two or more spectrum measurements at each position of the object light beam may be performed. The spectra are measured in the way, that phase of the interference fringes between neighbouring spectra form a fraction of the wave length. In contemporary systems, reference mirrors mounted on the positioning device are used, which give only a small delay in the reference light beam relative to the object light beam that takes place in the shifting of the interference fringes. In the proposed variant of the apparatus for complex measurement, instead of the phase-change, thanks to the movement of the reference mirror, the phase changes are achieved by changes in the position of the components of the optical frequency comb in the domain of k. The creation of images using this method has been described in several publications and is realised using mathematical methods, by which information regarding the phase and amplitude of the interference fringes may be obtained.

The invention claimed is:

1. An apparatus for imaging of objects by applying optical frequency domain tomography and provided with an adjusting system for setting a relative position of photosensitive elements and a spectrum image, and comprising a generating device emitting a light beam with a defined spectrum, a means for splitting the light beam into at least one object light beam and at least one reference light beam, a device forming a resultant light beam from the at least one reference light beam and the at least one object light beam and at least one device for spectral analysis of a light beam with a dispersion device, a set of optical elements, and a detection device of the spectrum, the detection device consisting of a single line of detectors, wherein the adjusting system is an automatically controlled device causing a relative angular displacement between at least one photosensitive element of the detection device and the spectrum image perpendicular to a propagation direction of the resultant light beam, the adjusting system further comprising at least one actuator acting to angularly displace at least one photosensitive element of the detection device, and movement of the at least one actuator causes the relative angular displacement between the at least one photosensitive element of the detection device of the spectrum and the spectrum image of the resultant light beam formed from the at least one reference light beam and the at least one object light beam split by the means for splitting the light beam with the defined spectrum emitted by the generating device.

2. A system for adjusting an apparatus for imaging of objects by applying optical frequency domain tomography provided with at least one device for spectral analysis of a light beam with a dispersion device, a set of optical elements, a detection device of the spectrum, the detection device consisting of a single line of detectors, and an automatically controlled device configured to cause a relative angular displacement between at least one photosensitive element of the detection device and the spectrum image perpendicular to a propagation direction of the resultant light beam, the automatically controlled device further comprising at least one actuator acting to angularly displace at least one photosensitive element of the detection device wherein movement of the actuator causes the relative angular displacement between the at least one photosensitive element of the detection device of the spectrum and the spectrum image.

3. A method for imaging of objects and a method for adjusting apparatus for optical frequency domain tomography provided with a generating device emitting a light beam with a defined spectrum, a means for splitting the light beam into at least one object light beam and at least one reference light beam, a device forming a resultant light beam from the at least one object light beam and the at least one reference light beam, an adjusting system, at least one device for spectral analysis of the resultant light beam and having a dispersion device for splitting the resultant light beam into a spectrum of the resultant light beam, a set of optical elements for forming or directing the resultant light beam and a detection device of the spectrum with at least one photosensitive element for registering the spectrum of resultant light beam, the detection device consisting of a single line of detectors, wherein the at least one photosensitive element of the detection device of the resultant light beam and an image of the spectrum are angularly displaced relative to each other in a plane perpendicular to a propagation direction of the resultant light beam using at least one actuator acting to angularly displace at least one photosensitive element of the detection device.

4. The method according to claim 3 wherein when displacing the at least one photosensitive element of the detection device of the resultant light beam and the image of the spectrum relative to each other using the actuator, the detection device and a line of the image of the spectrum are brought to cross each other, a point of change-over is determined at the detection device, a direction of rotation, in the plane perpendicular to the propagation direction of the resultant light beam, of either the at least one photosensitive element relative to the image of the resultant light beam or of the image of the resultant light beam relative to the at least one photosensitive element is changed after crossing the point of change-over by the line of the image of the spectrum, and the direction of rotation is changed until parameters of registration of the spectrum either determined by a manufacturer of the apparatus for optical frequency domain tomography or recognized by a user as sufficient for registration of the spectrum are achieved.

5. The method according to claim 3 wherein the at least one photosensitive element is displaced relative to the image of the resultant light beam until an electric signal is generated by the detection device, after determining a point of change-over on the detection device, a direction of rotation of the at least one photosensitive element of the detection device relative to the image of the resultant light beam or of the image of the resultant light beam relative to the at least one photosensitive element of the detection device is changed at every crossing of the point of change-over by the line of the image of the spectrum, and the direction of rotation is changed until either a curve of light intensity I or energy registered by the detection device versus wave length $\lambda$ achieves a shape corresponding to a shape of a curve of light intensity I or energy of the light emitted by the light source versus wave length $\lambda$ or area under the curve of light intensity I or energy registered by the detection device versus wave length $\lambda$ achieves area corresponding to the area under the curve of light intensity I emitted by the light source after taking into account scattering loss.

* * * * *